(12) United States Patent
Frampton et al.

(10) Patent No.: US 12,331,748 B2
(45) Date of Patent: Jun. 17, 2025

(54) NOISE AND VIBRATION MANAGEMENT FOR SMOKE EVACUATION SYSTEM

(71) Applicant: Megadyne Medical Products, Inc., Draper, UT (US)

(72) Inventors: Chad S. Frampton, American Fork, UT (US); Shawn K. Horner, Woods Cross, UT (US); Darcy W. Greep, Herriman, UT (US); Frederick Shelton, Hillsboro, OH (US); Jason Harris, Lebanon, OH (US); David Yates, West Chester, OH (US); Roger Millis, West Jordan, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 5 days.

(21) Appl. No.: 18/346,675

(22) Filed: Jul. 3, 2023

(65) Prior Publication Data

US 2023/0340958 A1    Oct. 26, 2023

Related U.S. Application Data

(63) Continuation of application No. 15/826,370, filed on Nov. 29, 2017, now Pat. No. 11,725,664.

(51) Int. Cl.
*F04C 29/06* (2006.01)
*A61B 18/14* (2006.01)
(Continued)

(52) U.S. Cl.
CPC ............. *F04C 29/06* (2013.01); *A61B 18/14* (2013.01); *A61M 1/80* (2021.05); *F04C 18/0207* (2013.01);
(Continued)

(58) Field of Classification Search
CPC ...... F04C 29/06; F04C 18/0207; F04C 18/12; F04C 18/0215; F04C 28/08;
(Continued)

(56) References Cited

U.S. PATENT DOCUMENTS 1,165,288 A    12/1915  Rimmer
1,789,194 A    1/1931   Rockwell
(Continued)

FOREIGN PATENT DOCUMENTS

CN    204312376 U    5/2015
CN    304909540 S    11/2018
(Continued)

OTHER PUBLICATIONS

Examiner Interview Summary Record (PTOL-413) Mailed on Mar 17, 2022 for U.S. Appl. No. 15/826,370, 2 page(s).
(Continued)

*Primary Examiner* — Charles G Freay
*Assistant Examiner* — Lilya Pekarskaya
(74) *Attorney, Agent, or Firm* — Workman Nydegger

(57) ABSTRACT

A system for noise and vibration management of a smoke evacuation system includes a pump that compresses air and produces a pressure differential within an airflow path. The pump may be a sealed, positive displacement pump. The system includes vibration absorption mechanisms disposed between inner and outer housings, as well as on the outside surface of the outer housing. Methods of controlling and regulating a motor of the system to preserve the lifespan of the motor and maintain consistent airflow rates throughout the smoke evacuation system include varying a supply of electrical current to the motor so that it can operate at variable performance levels. Orifices are opened and closed in order to relieve resistance pressures within the airflow path due to clogging and blockages.

12 Claims, 16 Drawing Sheets

(51) Int. Cl.
  *A61M 1/00* (2006.01)
  *F04C 18/02* (2006.01)
  *F04C 18/12* (2006.01)
  *F04C 28/08* (2006.01)
  *F04C 29/00* (2006.01)
  *A61B 18/00* (2006.01)
  *A61B 18/12* (2006.01)
  *A61B 18/16* (2006.01)

(52) U.S. Cl.
  CPC .......... *F04C 18/0215* (2013.01); *F04C 18/12* (2013.01); *F04C 28/08* (2013.01); *F04C 29/0085* (2013.01); *A61B 2018/00595* (2013.01); *A61B 2018/00601* (2013.01); *A61B 18/1206* (2013.01); *A61B 18/16* (2013.01); *A61B 2218/008* (2013.01); *A61M 1/73* (2021.05); *A61M 2202/02* (2013.01); *A61M 2205/103* (2013.01); *A61M 2205/42* (2013.01); *A61M 2205/75* (2013.01); *F04C 29/0071* (2013.01); *F04C 2240/40* (2013.01); *F04C 2270/051* (2013.01); *F04C 2270/125* (2013.01); *F04C 2270/135* (2013.01)

(58) Field of Classification Search
  CPC ............ F04C 29/0085; F04C 2270/135; F04C 29/0071; F04C 2240/40; F04C 2270/051; A61B 18/14; A61B 2218/08; A61B 18/1206; A61B 2018/00595; A61B 2018/00601; A61B 18/16; A61M 1/0066; A61M 1/0025; A61M 2202/02; A61M 2205/103; A61M 2205/42; A61M 2205/75
  See application file for complete search history.

(56) References Cited

U.S. PATENT DOCUMENTS

| | | | |
|---|---|---|---|
| 2,577,606 A | 12/1951 | Conley | |
| 3,815,752 A | 6/1974 | Hoffman et al. | |
| 3,841,490 A | 10/1974 | Hoffman et al. | |
| 4,116,649 A | 9/1978 | Cullen et al. | |
| 4,157,234 A | 6/1979 | Shaffer et al. | |
| 4,396,206 A | 8/1983 | Tsuge et al. | |
| 4,619,672 A | 10/1986 | Robertson | |
| 4,642,128 A | 2/1987 | Solorzano | |
| D291,353 S | 8/1987 | Conero et al. | |
| 4,701,193 A * | 10/1987 | Robertson | B01D 46/4245 96/380 |
| 4,786,298 A | 11/1988 | Billiet et al. | |
| 4,788,298 A | 11/1988 | Wang | |
| 4,810,269 A | 3/1989 | Stackhouse et al. | |
| 4,826,513 A | 5/1989 | Stackhouse et al. | |
| 4,986,839 A | 1/1991 | Wertz et al. | |
| 4,988,839 A | 1/1991 | Kennicott | |
| D315,410 S | 3/1991 | Aten | |
| 5,108,389 A | 4/1992 | Cosmescu | |
| 5,144,176 A | 9/1992 | Popper | |
| 5,144,178 A | 9/1992 | Sugiura | |
| 5,160,334 A | 11/1992 | Billings et al. | |
| 5,221,192 A | 6/1993 | Heflin et al. | |
| 5,226,939 A | 7/1993 | Nicolas et al. | |
| 5,228,939 A | 7/1993 | Chu | |
| 5,242,474 A * | 9/1993 | Herbst | A61B 18/00 55/467 |
| 5,288,469 A | 2/1994 | Skalla | |
| 5,288,489 A | 2/1994 | Reich et al. | |
| 5,318,516 A | 6/1994 | Cosmescu | |
| 5,336,218 A | 8/1994 | Linhares | |
| 5,342,349 A | 8/1994 | Kaufman | |
| D357,738 S | 4/1995 | Kaufman | |
| 5,423,779 A | 6/1995 | Yeh | |
| 5,431,650 A | 7/1995 | Cosmescu | |
| 5,456,248 A | 10/1995 | Holian et al. | |
| 5,507,859 A | 4/1996 | Kaiser | |
| 5,522,808 A | 6/1996 | Skalla | |
| 5,597,385 A | 1/1997 | Moerke | |
| 5,619,992 A | 4/1997 | Guthrie et al. | |
| 5,620,441 A | 4/1997 | Greff et al. | |
| 5,674,219 A | 10/1997 | Monson et al. | |
| 5,690,480 A | 11/1997 | Suzuki et al. | |
| 5,853,410 A | 12/1998 | Greff et al. | |
| 5,874,052 A | 2/1999 | Holland | |
| 5,910,291 A | 6/1999 | Skalla et al. | |
| 5,947,694 A * | 9/1999 | Hablanian | F04C 25/02 418/5 |
| 5,992,413 A | 11/1999 | Martin et al. | |
| D420,140 S | 2/2000 | Noble et al. | |
| 6,050,792 A | 4/2000 | Shaffer | |
| 6,089,527 A | 7/2000 | Utterberg | |
| 6,110,259 A | 8/2000 | Schultz et al. | |
| 6,129,530 A | 10/2000 | Shaffer | |
| 6,145,509 A | 11/2000 | Tanner | |
| 6,203,590 B1 | 3/2001 | Byrd et al. | |
| 6,203,762 B1 | 3/2001 | Skalla et al. | |
| 6,331,246 B1 | 12/2001 | Beckham et al. | |
| 6,439,864 B1 | 8/2002 | Shaffer | |
| D467,654 S | 12/2002 | Klug et al. | |
| 6,511,308 B2 | 1/2003 | Shaffer | |
| 6,524,307 B1 | 2/2003 | Palmerton et al. | |
| 6,544,210 B1 | 4/2003 | Trudel et al. | |
| 6,585,791 B1 | 7/2003 | Garito et al. | |
| 6,589,316 B1 | 7/2003 | Schultz et al. | |
| 6,589,318 B2 | 7/2003 | El-Shoubary et al. | |
| 6,592,543 B1 | 7/2003 | Wortrich et al. | |
| 6,616,722 B1 | 9/2003 | Cartellone | |
| 6,663,698 B2 | 12/2003 | Mishin et al. | |
| D485,339 S | 1/2004 | Klug et al. | |
| 6,709,248 B2 | 3/2004 | Fujioka et al. | |
| 6,736,620 B2 | 5/2004 | Satoh | |
| 6,758,885 B2 | 7/2004 | Leffel et al. | |
| 6,786,707 B2 | 9/2004 | Kim | |
| D513,314 S | 12/2005 | Iddings et al. | |
| 7,014,434 B2 | 3/2006 | Fujioka et al. | |
| D521,137 S | 5/2006 | Khalil | |
| D545,955 S | 7/2007 | Arias | |
| 7,258,712 B2 | 8/2007 | Schultz et al. | |
| D553,228 S | 10/2007 | Virr et al. | |
| 7,276,052 B2 | 10/2007 | Kobayashi et al. | |
| D555,803 S | 11/2007 | Garito et al. | |
| 7,294,116 B1 | 11/2007 | Ellman et al. | |
| D568,991 S | 5/2008 | Schweikert et al. | |
| D574,323 S | 8/2008 | Waaler | |
| 7,465,156 B2 * | 12/2008 | Lee | F04B 39/0044 417/363 |
| 7,497,340 B2 | 3/2009 | Hershberger et al. | |
| 7,597,731 B2 | 10/2009 | Palmerton et al. | |
| D608,447 S | 1/2010 | Meyer et al. | |
| D616,986 S | 6/2010 | Biegen et al. | |
| D625,399 S | 10/2010 | Horiguchi | |
| D626,204 S | 10/2010 | Morgan | |
| 7,819,957 B2 | 10/2010 | Roberts et al. | |
| 7,942,655 B2 | 5/2011 | Shaffer | |
| D646,368 S | 10/2011 | Osendorf et al. | |
| 8,033,798 B2 | 10/2011 | Suh et al. | |
| D648,841 S | 11/2011 | Lam | |
| 8,142,175 B2 | 3/2012 | Duppert et al. | |
| D657,468 S | 4/2012 | Held | |
| 8,147,577 B2 | 4/2012 | Palmerton et al. | |
| 8,190,398 B2 | 5/2012 | Kitaguchi et al. | |
| D666,704 S | 9/2012 | Osendorf et al. | |
| 8,298,420 B2 | 10/2012 | Burrows | |
| 8,556,570 B2 | 10/2013 | Ishihara | |
| 8,608,816 B2 | 12/2013 | Palmerton et al. | |
| 8,684,705 B2 | 4/2014 | Magoon et al. | |
| 8,727,744 B2 | 5/2014 | Magoon et al. | |
| 8,974,569 B2 | 3/2015 | Matula et al. | |
| 9,011,366 B2 | 4/2015 | Dean et al. | |
| 9,028,230 B2 | 5/2015 | Shaffer | |
| 9,067,030 B2 | 6/2015 | Stearns et al. | |
| 9,074,598 B2 | 7/2015 | Shaffer et al. | |
| D736,933 S | 8/2015 | Qiu et al. | |
| D737,449 S | 8/2015 | Zheng et al. | |

(56) References Cited

U.S. PATENT DOCUMENTS

| | | |
|---|---|---|
| D739,770 S | 9/2015 | Scampoli et al. |
| 9,199,047 B2 | 12/2015 | Stearns et al. |
| 9,215,964 B2 | 12/2015 | Loske |
| 9,215,984 B2 | 12/2015 | Hattery et al. |
| 9,366,254 B2 | 6/2016 | Murakami |
| 9,387,295 B1 | 7/2016 | Mastri et al. |
| 9,387,296 B1 | 7/2016 | Mastri et al. |
| D764,649 S | 8/2016 | Ko et al. |
| 9,415,160 B2 | 8/2016 | Bonano et al. |
| 9,435,339 B2 | 9/2016 | Calhoun et al. |
| 9,474,512 B2 | 10/2016 | Blackhurst et al. |
| 9,532,843 B2 | 1/2017 | Palmerton et al. |
| 9,549,849 B2 | 1/2017 | Charles |
| 9,579,428 B1 | 2/2017 | Reasoner et al. |
| D783,178 S | 4/2017 | Mead et al. |
| D799,055 S | 10/2017 | Kennedy et al. |
| D802,024 S | 11/2017 | Aoki |
| 9,867,914 B2 | 1/2018 | Bonano et al. |
| 9,943,355 B2 | 4/2018 | Babini et al. |
| D844,333 S | 4/2019 | Maynard |
| D868,236 S | 11/2019 | Frampton et al. |
| D868,287 S | 11/2019 | Frampton |
| 10,631,916 B2 | 4/2020 | Horner et al. |
| D886,976 S | 6/2020 | Horner et al. |
| D890,900 S | 7/2020 | Bink et al. |
| 10,758,293 B2 | 9/2020 | Horner et al. |
| 10,758,855 B2 | 9/2020 | Horner et al. |
| 10,758,856 B2 | 9/2020 | Horner et al. |
| D912,762 S | 3/2021 | Horner et al. |
| D943,058 S | 2/2022 | Horner et al. |
| 11,305,223 B2 | 4/2022 | Horner et al. |
| 11,389,225 B2 | 7/2022 | Frampton et al. |
| D967,384 S | 10/2022 | Horner |
| 2004/0223859 A1 | 11/2004 | Sharp |
| 2005/0000196 A1 | 1/2005 | Schultz |
| 2005/0189283 A1 | 9/2005 | Smit et al. |
| 2005/0263004 A1 | 12/2005 | Larsen et al. |
| 2006/0099096 A1 | 5/2006 | Shaffer et al. |
| 2006/0224150 A1 | 10/2006 | Arts et al. |
| 2007/0066970 A1 | 3/2007 | Ineson |
| 2009/0022613 A1 | 1/2009 | Dai et al. |
| 2010/0185139 A1 | 7/2010 | Stearns et al. |
| 2011/0067699 A1 | 3/2011 | Caruso et al. |
| 2011/0203585 A1 | 8/2011 | Cozean et al. |
| 2013/0023160 A1 | 1/2013 | Healey et al. |
| 2013/0115122 A1 | 5/2013 | Lee |
| 2013/0231606 A1 | 9/2013 | Stearns et al. |
| 2013/0251514 A1 | 9/2013 | Oakman |
| 2014/0356207 A1 | 12/2014 | Yang |
| 2015/0133750 A1 | 5/2015 | White et al. |
| 2015/0224237 A1 | 8/2015 | Reasoner et al. |
| 2015/0273381 A1 | 10/2015 | Stoner et al. |
| 2016/0000494 A1 | 1/2016 | Cosmescu |
| 2016/0001102 A1 | 1/2016 | Huh |
| 2016/0169941 A1 | 6/2016 | Fukui |
| 2016/0287817 A1 | 10/2016 | Mastri et al. |
| 2016/0327042 A1* | 11/2016 | Shaffer ............. F04C 23/001 |
| 2016/0367266 A1 | 12/2016 | Palmerton et al. |
| 2017/0014557 A1 | 1/2017 | Minskoff et al. |
| 2017/0014560 A1* | 1/2017 | Minskoff ............. A61M 1/76 |
| 2017/0095603 A1 | 4/2017 | Cho |
| 2017/0165725 A1 | 6/2017 | Hersey et al. |
| 2017/0181768 A1 | 6/2017 | Galley |
| 2017/0181788 A1 | 6/2017 | Dastjerdi et al. |
| 2017/0274125 A1 | 9/2017 | Minskoff et al. |
| 2019/0001029 A1* | 1/2019 | Davie ................ A61M 1/65 |
| 2019/0159825 A1 | 5/2019 | Frampton et al. |
| 2019/0159826 A1 | 5/2019 | Horner et al. |
| 2019/0159827 A1 | 5/2019 | Horner et al. |
| 2019/0159830 A1 | 5/2019 | Horner et al. |
| 2019/0160409 A1 | 5/2019 | Horner et al. |
| 2019/0160410 A1 | 5/2019 | Horner et al. |
| 2019/0162186 A1 | 5/2019 | Frampton et al. |
| 2020/0214760 A1 | 7/2020 | Horner et al. |
| 2020/0324238 A1 | 10/2020 | Jones et al. |
| 2020/0353399 A1 | 11/2020 | Horner et al. |
| 2021/0199136 A1 | 7/2021 | Tulett et al. |
| 2022/0409261 A1 | 12/2022 | Horner et al. |

FOREIGN PATENT DOCUMENTS

| | | |
|---|---|---|
| GB | 2117982 A | 10/1983 |
| JP | 2016-148281 A | 8/2016 |
| PL | 220478 B1 | 10/2015 |
| WO | 94/08698 A1 | 4/1994 |
| WO | 2016/142690 A1 | 9/2016 |
| WO | 2017/003712 A1 | 1/2017 |
| WO | 2017/066720 A1 | 4/2017 |
| WO | 2017/112684 A1 | 6/2017 |
| WO | 2017/177069 A1 | 10/2017 |

OTHER PUBLICATIONS

Examiner Interview Summary Record (PTOL-413) Mailed on Nov. 27, 2020 for U.S. Appl. No. 15/826,370, 2 page(s).
Final Rejection Mailed on Feb. 24, 2021 for U.S. Appl. No. 15/826,370, 29 page(s).
Final Rejection Mailed on Jul. 22, 2022 for U.S. Appl. No. 15/826,370, 39 page(s).
List of references cited by examiner Mailed on Aug. 18, 2020 for U.S. Appl. No. 15/826,370, 1 page(s).
List of references cited by examiner Mailed on Jul. 22, 2022 for U.S. Appl. No. 15/826,370, 1 page(s).
List of references cited by examiner Mailed on Mar. 3, 2021 for U.S. Appl. No. 15/826,376, 1 page(s).
Non-Final Rejection Mailed on Apr. 26, 2021 for U.S. Appl. No. 15/826,376, 7 page(s).
Non-Final Rejection Mailed on Aug. 18, 2020 for U.S. Appl. No. 15/826,370, 24 page(s).
Non-Final Rejection Mailed on Jan. 26, 2023 for U.S. Appl. No. 15/826,370, 9 page(s).
Non-Final Rejection Mailed on Nov. 23, 2021 for U.S. Appl. No. 15/826,370, 35 page(s).
Notice of Allowance and Fees Due (PTOL-85) Mailed on Apr. 14, 2023 for U.S. Appl. No. 15/826,370, 6 page(s).
Notice of Allowance and Fees Due (PTOL-85) Mailed on Dec. 15, 2021 for U.S. Appl. No. 15/826,376, 4 page(s).
Notice of Allowance and Fees Due (PTOL-85) Mailed on Mar. 3, 2021 for U.S. Appl. No. 15/826,376, 8 page(s).
Notice of Allowance and Fees Due (PTOL-85) Mailed on Mar. 29, 2023 for U.S. Appl. No. 15/826,370, 9 page(s).
Notice of Allowance and Fees Due (PTOL-85) Mailed on Oct. 1, 2021 for U.S. Appl. No. 15/826,376, 8 page(s).
Office Action Appendix Mailed on Mar. 17, 2022 for U.S. Appl. No. 15/826,370, 1 page(s).
Requirement for Restriction/Election Mailed on Feb. 13, 2020 for U.S. Appl. No. 15/826,370, 9 page(s).
Requirement for Restriction/Election Mailed on Sep. 30, 2020 for U.S. Appl. No. 15/826,376, 6 page(s).
Notice of Allowance received for U.S. Appl. No. 16/825,998, mailed on Oct. 22, 2021, 2 pages.
Notice of Allowance received for U.S. Appl. No. 29/733,877, mailed on Dec. 27, 2021, 2 pages.
Notice of Allowance received for U.S. Appl. No. 29/733,877, mailed on Sep. 2, 2021, 9 pages.
Notice of Allowance received for U.S. Appl. No. 29/760,171, mailed on Feb. 24, 2022, 6 pages.
Notice of Allowance received for U.S. Appl. No. 29/760,171, mailed on Jun. 10, 2022, 6 pages.
Requirement for Restriction/Election received for U.S. Appl. No. 15/826,289, mailed on Dec. 15, 2020, 8 pages.
Requirement for Restriction/Election received for U.S. Appl. No. 15/826,376, mailed on Sep. 30, 2020, 6 pages.
Requirement for Restriction/Election received for U.S. Appl. No. 29/760,171, mailed on Jan. 13, 2022, 5 pages.
U.S. Appl. No. 16/825,998, filed Mar. 20, 2020.
U.S. Appl. No. 29/627,793, filed Nov. 29, 2017.
U.S. Appl. No. 29/627,794, filed Nov. 29, 2017.

(56) References Cited

OTHER PUBLICATIONS

"Megadyne Surgical Smoke Evacuation System found online [Sep. 11, 2018]—http://www.hcp-austria.com/Minivac%20Smoke%20Evacuators.html".
Bovie 35 hour filter found online [Sep. 11, 2018]—http://www.boviemedical.com/smoke-shark-ii/.
Chinese Patent Application No. 201830176822, filed on Apr. 2018.
Chinese Patent Application No. 304909540, filed Apr. 25, 2018.
Exam Report for MX/f/2018/001583 mailed Jan. 20, 2020.
Examiner Interview Summary received for U.S. Appl. No. 15/826,370, mailed on Nov. 27, 2020, 2 pages.
Final Office Action for U.S. Appl. No. 15/826,287 mailed Dec. 20, 2019.
Final Office Action for U.S. Appl. No. 15/826,342 mailed Nov. 5, 2019.
Final Office Action received for U.S. Appl. No. 15/826,289, mailed on Oct. 5, 2021, 10 pages.
Final Office Action received for U.S. Appl. No. 15/826,370, mailed on Feb. 24, 2021, 31 pages.
Final Office Action received for U.S. Appl. No. 15/826,370, mailed on Jul. 22, 2022, 40 pages.
International Search and Written Opinion for PCT/IB2018/059376 mailed May 7, 2019.
International Search Report and Written Opinion for PCT/IB2018/059371 mailed Feb. 15, 2019.
International Search Report and Written Opinion for PCT/IB2018/059375 mailed May 7, 2019.
International Search Report and Written Opinion for PCT/IB2018/059377 mailed Mar. 6, 2019.
International Search Report and Written Opinion for PCT/IB2018/059378 mailed May 10, 2019.
Non-Final Office Action for U.S. Appl. No. 15/826,287 mailed Jul. 17, 2019.
Non-Final Office Action for U.S. Appl. No. 15/826,325 mailed Aug. 1, 2019.
Non-Final Office Action for U.S. Appl. No. 15/826,342 mailed Jul. 16, 2019.
Non-Final Office Action for U.S. Appl. No. 15/826,344 mailed Sep. 12, 2019.
Non-Final Office Action for U.S. Appl. No. 29/627,788 mailed Feb. 19, 2019.
Non-Final Office Action for U.S. Appl. No. 29/627,793 mailed on Oct. 29, 2018.
Non-Final Office Action for U.S. Appl. No. 29/627,794 mailed Feb. 19, 2020.
Non-Final Office Action for U.S. Appl. No. 29/627,794 mailed Jul. 10, 2019.
Non-Final Office Action received for U.S. Appl. No. 15/826,289, mailed on May 28, 2021, 12 pages.
Non-Final Office Action Received for U.S. Appl. No. 15/826,370, Mailed on Aug. 18, 2020, 24 pages.
Non-Final Office Action received for U.S. Appl. No. 15/826,370, mailed on Jan. 26, 2023, 9 pages.
Non-Final Office Action received for U.S. Appl. No. 15/826,370, mailed on Nov. 23, 2021, 35 pages.
Non-Final Office Action received for U.S. Appl. No. 15/826,376, mailed on Apr. 26, 2021, 7 pages.
Non-Final Office Action received for U.S. Appl. No. 16/825,998, mailed on Feb. 2, 2021, 9 pages.
Non-Final Office Action received for U.S. Appl. No. 16/937,000, mailed on Aug. 31, 2021, 8 pages.
Notice of Allowance for U.S. Appl. No. 15/826,344 mailed May 21, 2020.
Notice of Allowance for U.S. Appl. No. 29/627,794 mailed Aug. 14, 2020.
Notice of Allowance for U.S. Appl. No. 15/826,287 mailed Feb. 12, 2020.
Notice of Allowance for U.S. Appl. No. 15/826,325 mailed Dec. 26, 2019.
Notice of Allowance for U.S. Appl. No. 15/826,342 mailed Apr. 23, 2020.
Notice of Allowance for U.S. Appl. No. 15/826,342 mailed Jan. 31, 2020.
Notice of Allowance for U.S. Appl. No. 15/826,344 mailed Apr. 22, 2020.
Notice of Allowance for U.S. Appl. No. 15/826,344 mailed Jan. 23, 2020.
Notice of Allowance for U.S. Appl. No. 16/937,000 mailed Dec. 17, 2021.
Notice of Allowance for U.S. Appl. No. 29/627,788 mailed Jul. 23, 2019.
Notice of Allowance for U.S. Appl. No. 29/627,793 mailed Feb. 21, 2020.
Notice of Allowance for U.S. Appl. No. 15/826,344 dated Apr. 22, 2020.
Notice of Allowance received for U.S. Appl. No. 15/826,289, mailed on Mar. 18, 2022, 8 pages.
Notice of Allowance received for U.S. Appl. No. 15/826,370, mailed on Apr. 14, 2023, 6 pages.
Notice of Allowance received for U.S. Appl. No. 15/826,376, mailed on Mar. 3, 2021, 9 pages.
Notice of Allowance received for U.S. Appl. No. 15/826,376, mailed on Oct. 1, 2021, 8 pages.
Notice of Allowance received for U.S. Appl. No. 16/825,998, mailed on Apr. 6, 2021, 9 pages.
Notice of Allowance received for U.S. Appl. No. 16/825,998, mailed on Jul. 27, 2021, 10 pages.

\* cited by examiner

| | Pressure Increase | Operational Pressure | Pressure Ratio | Air Volume |
|---|---|---|---|---|
| Fan | Low Increase | Atm - 1.5psig | below 1.1 | High |
| Blower | Moderate Increase | 1.5psig - 2.72 psig | 1.11-1.20 | Very High |
| Compressor | High Increase | >2.72psig | >2.0 | Low |

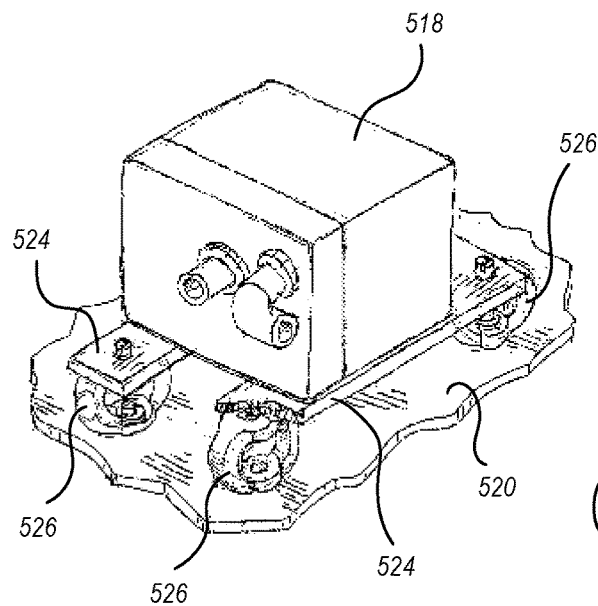 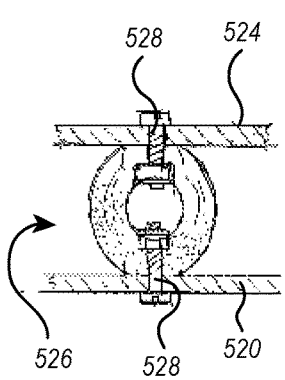 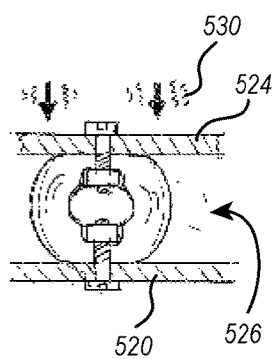
FIG. 13A          FIG. 13B          FIG. 13C
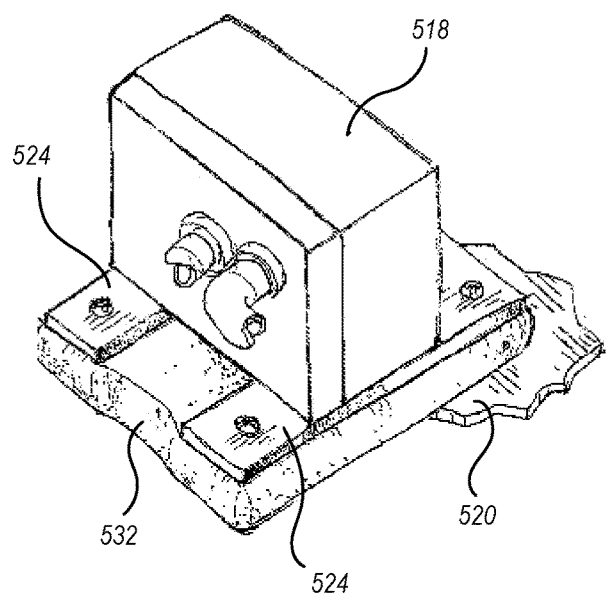 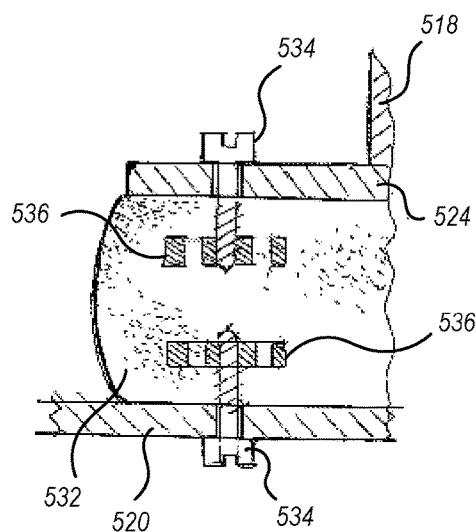
FIG. 14A          FIG. 14B

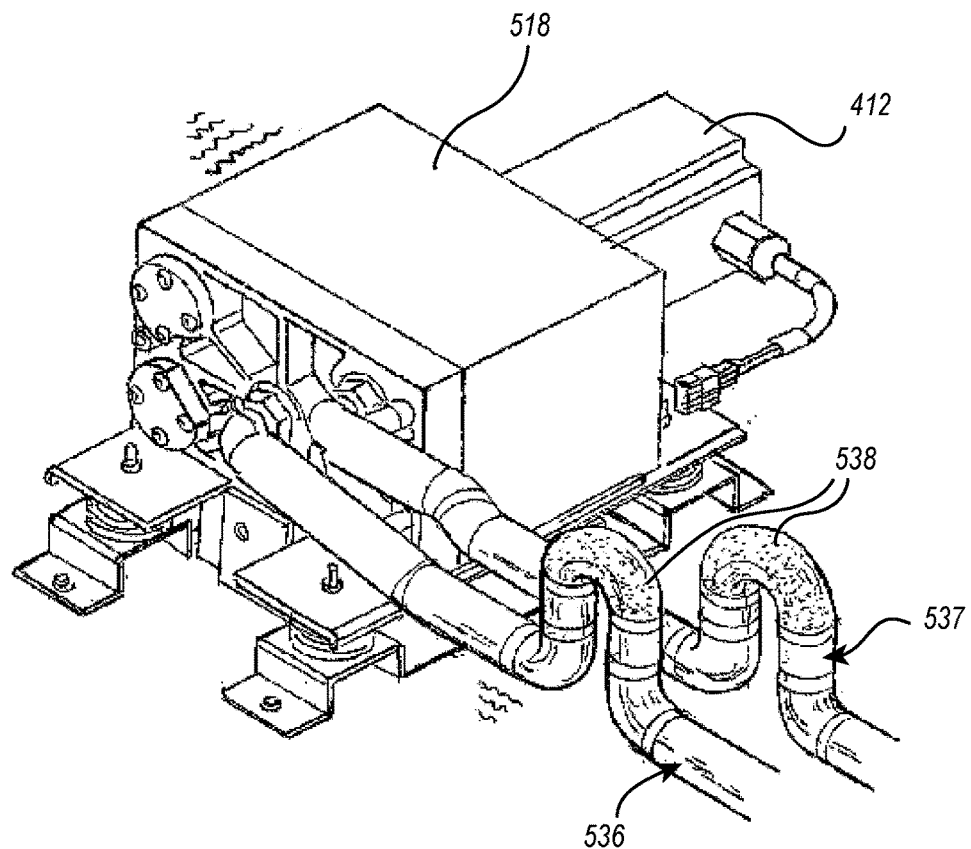
FIG. 15
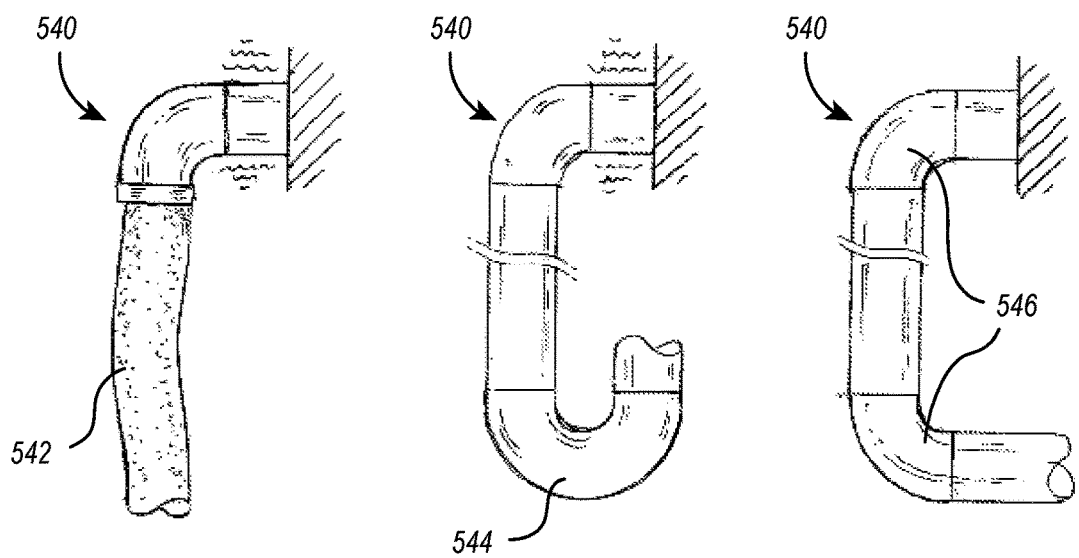
FIG. 16A     FIG. 16B     FIG. 16C

NOISE AND VIBRATION MANAGEMENT FOR SMOKE EVACUATION SYSTEM

CROSS-REFERENCE TO RELATED APPLICATIONS

This application is a continuation of U.S. patent application Ser. No. 15/826,370, filed Nov. 29, 2017, and entitled Noise and Vibration Management For Smoke Evacuation System, the entire content of which is incorporated herein by reference.

BACKGROUND

1. Technical Field

The present disclosure relates to smoke evacuation systems used in electrosurgical systems. More specifically, the present disclosure relates to apparatus and methods of dampening vibrations and noise caused by a smoke evacuation system.

2. The Relevant Technology

As is known to those skilled in the art, modern surgical techniques typically employ radio frequency (RF) power to cut tissue and coagulate bleeding encountered in performing surgical procedures. Such electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cutting and cauterization result in smoke released into the air that can be unpleasant and obstructive of the view of a practitioner. Many electrosurgical systems may therefore employ a smoke evacuation system that captures the resulting smoke and directs it through a filter and exhaust port, away from practitioners and/or patients.

Smoke evacuation systems typically comprise a fan and a filter. The fan creates suction that draws smoke through a vacuum tube into the filter. A vacuum tube may terminate at the hand piece that includes the electrode tip so that the smoke is sucked in at the hand piece. Other electrosurgical systems may include separate hand pieces that are used to suck the smoke into the system. The smoke travels to the filter via a vacuum tube and offensive smells are filtered out as the smoke moves through the filter. Filtered air may then exit the smoke evacuation system as exhaust.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to smoke evacuation systems. More specifically, the present disclosure relates to methods and apparatuses for managing noise and vibrations of smoke evacuation systems. Noise and vibrations produced by smoke evacuation systems can be distracting and irritating to practitioners performing surgery. The present disclosure relates to methods and apparatuses for reducing noise and vibrations associated with smoke evacuation systems.

In one embodiment, a smoke evacuation system includes a filter, a pump that has a sealed positive displacement airflow path, and a motor that drives the pump. The sealed positive displacement airflow path of the pump may comprise one or more circulation paths of a gas within the pump. In one embodiment, the pump has a first operating pressure and a second operating pressure. The flow rate of a gas being pumped may be the same regardless of the operating pressure. The pump may compress incoming gas to create a pressure difference between various zones of airflow within the smoke evacuation system.

In one embodiment, a smoke evacuation system may include various vibration absorption mechanisms. The system may have a first housing enclosing the motor and the pump and a second housing enclosing the entire system. Vibration mechanisms may be disposed between the two housings and outside the second housing. Flexible tubing may also be incorporated to absorb vibrations.

A method of reducing the vibrations and noise of a smoke evacuation system may include regulating the motor engaged with the pump. The regulation of the motor may include varying a supply of current to the motor in order to operate the motor in at least two distinct operating levels. Regulation of the motor may depend on sensory inputs, such as temperature or pressure. Orifices may also be provided within the airflow path that allow communication with ambient surroundings of the system in order to relieve excessive resistance pressures in the system caused by blockages or clogging of the airflow path.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 13A illustrates one embodiment of vibration absorption mechanisms disposed between inner and outer housings;

FIGS. 13B and 13C illustrate various cross-sectional views of the vibration absorption mechanisms illustrated in FIG. 13A;

FIG. 14A illustrates one embodiment of a vibration absorption mechanism;

FIG. 14B illustrates a cross-sectional view of the vibration absorption mechanism illustrated in FIG. 14A;

FIG. 15 illustrates one embodiment of a vibration absorption mechanism;

FIGS. 16A through 16C illustrate various embodiments of vibration absorption mechanisms;

DETAILED DESCRIPTION

Introduction

The present disclosure relates to smoke evacuation systems. More specifically, the present disclosure relates to methods and apparatuses for managing noise and vibrations of smoke evacuation systems. Noise and vibrations produced by smoke evacuation systems can be distracting and irritating to practitioners performing surgery. The present disclosure relates to methods and apparatuses for reducing noise and vibrations associated with smoke evacuation systems.

Figure 1:
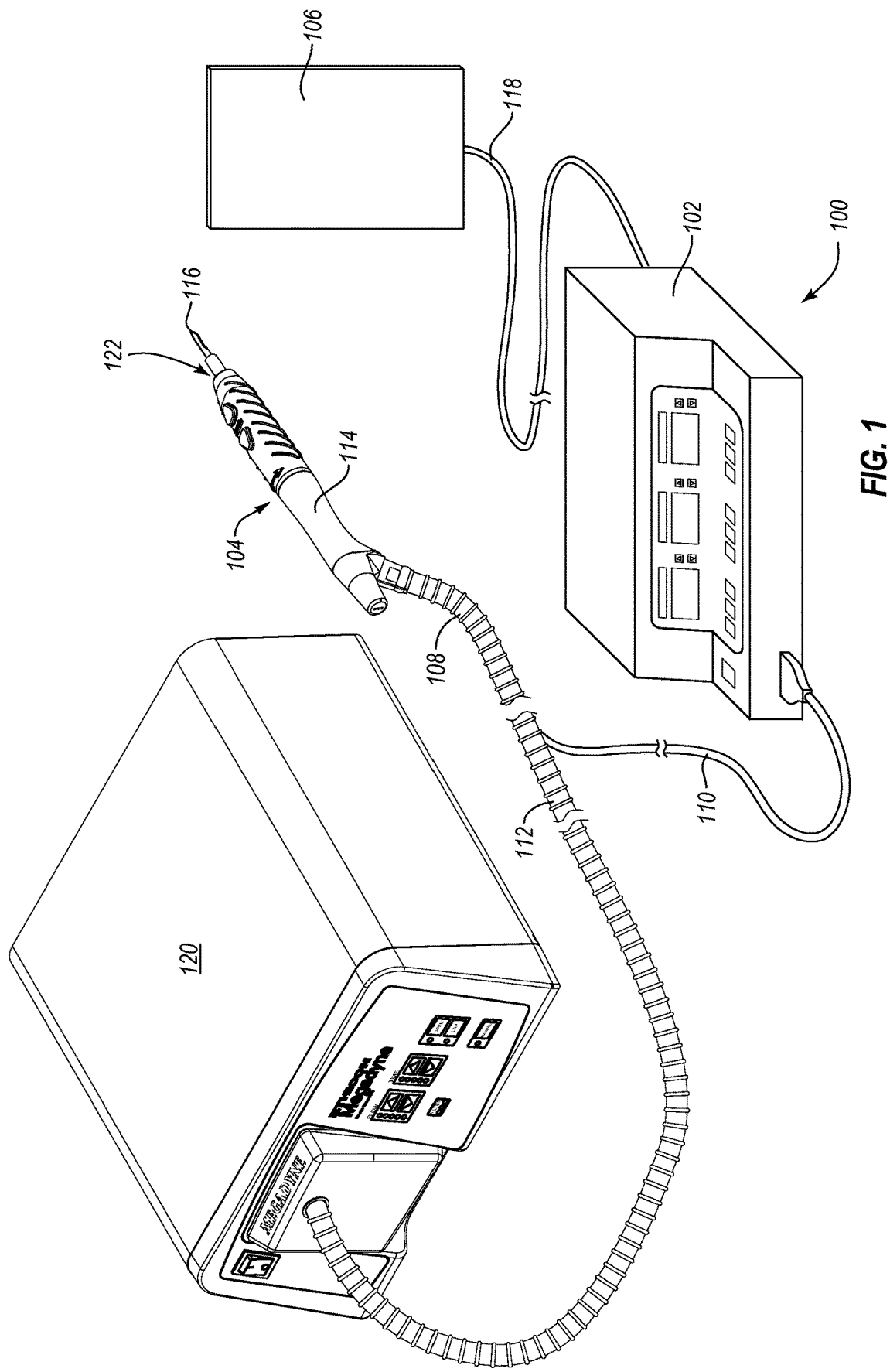
FIG. 1 illustrates an embodiment of an electrosurgical system.

FIG. 1 illustrates an exemplary electrosurgical system 100. The illustrated embodiment includes a signal generator 102, an electrosurgical instrument 104, a return electrode 106, and a smoke evacuation system 120. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with or adjacent to electrode tip 116. The tissue heating takes place at an appropriately high temperature to allow electrosurgical instrument 104 to be used to perform electrosurgery. Return electrode 106 is connected to generator 102 by a cable 118, and is either applied to or placed in close proximity to the patient (depending on the type of return electrode used), in order to complete the circuit and provide a return electrical path to wave generator 102 for energy that passes into the patient's body.

The heating of cellular matter of the patient by the electrode tip 116, or cauterization of blood vessels to prevent bleeding, results in smoke being released from the heated tissue. The electrosurgical instrument 104 may comprise a smoke evacuation conduit opening 122 near the electrode tip 116 so as to be able to capture the smoke that is released during a procedure. Vacuum suction may draw the smoke into the conduit opening 122, through the electrosurgical instrument 104, and into the vacuum hose 112 toward the smoke evacuation system 120.

Figure 2:
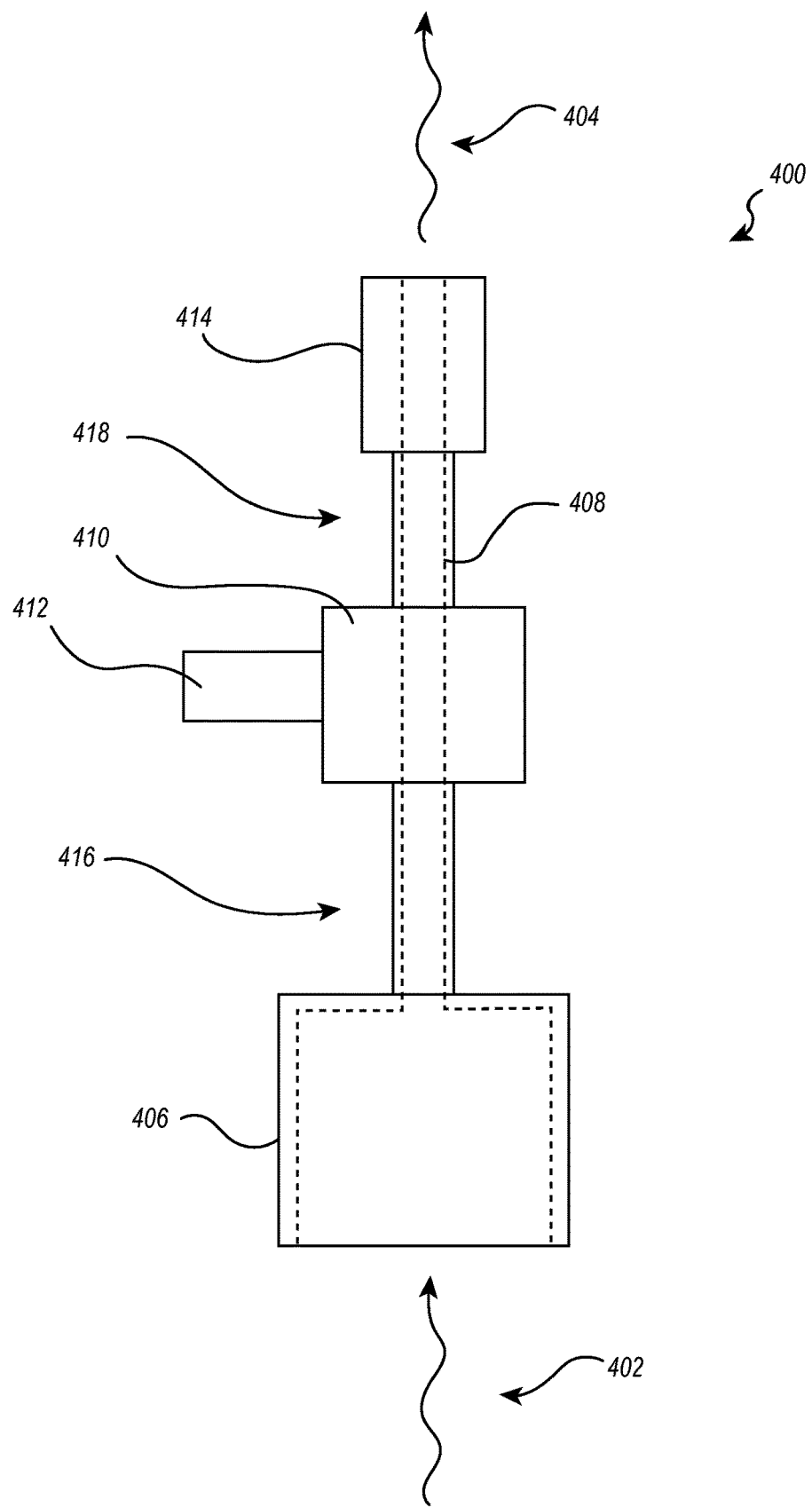
FIG. 2 illustrates a schematic of an embodiment of a smoke evacuation system.

FIG. 2 illustrates a schematic of an embodiment of a smoke evacuation system 400. The smoke evacuation system 400 may include a filter 406 and an airflow path 408. The airflow path 408 may comprise a pump 410 disposed in-line with the airflow path 408 producing a pressure difference within the airflow path 408 by mechanical action. This pressure difference may cause movement of a gas through the airflow path 408.

The airflow path 408 may be at least partially comprised of a tube or other conduit that substantially contains and/or isolates the air moving through the airflow path 408 from air outside the airflow path. For example, the first zone 416 of the airflow path 408 may comprise a tube through which the airflow path 408 extends between the filter 406 and the pump 410. The second zone 418 of the airflow path 408 may also comprise a tube through which the airflow path 408 extends between the pump 410 and the exhaust mechanism 414. The airflow path 408 also extends through the filter 406, pump 410, and exhaust mechanism 414 so that a continuous airflow path 408 extends through the smoke evacuation system 400.

The gas drawn through the airflow path 408 may be smoke 402, or the filtered air remaining after the smoke 402 has passed through the filter 406. A motor 412 drives the pump 410. The smoke evacuation system 400 may also include an exhaust mechanism 414 that may also be disposed in-line with the airflow path 408. The airflow path 408 may extend from the inlet port 245 to the outlet port 250 and pass through the filter 406, pump 410 and exhaust mechanism 414

Pumps

The pump 410 may cause a suction of smoke 402 that has travelled through the vacuum tube 112 illustrated in FIG. 1 to the filter illustrated in FIG. 2. The smoke 402 may be drawn to the filter 406 via a suction created by the pump 410 as discussed above. The pump 410 may create a pressure difference between a first zone 416 and a second zone 418 of the airflow path 408. This pressure difference causes the smoke 402 to travel into the filter 406, which is disposed at an inlet of the airflow path 408, through the airflow path 408, and out the exhaust mechanism 414, which is disposed at an outlet of the airflow path 408. The filter 406 may extract potentially harmful, foul, or otherwise unwanted particulates from the smoke 402.

The pump 410 may be disposed in-line with the airflow path 408, meaning the gas flowing through the system enters the pump 410 at one end and exits the pump 410 at the other end. The pump 410 may provide a sealed positive displacement airflow path. The pump 410 may produce the sealed positive displacement airflow path by trapping (sealing) a first volume of gas and decreasing that volume to a second smaller volume as the gas moves through the pump 410. Decreasing the volume of the trapped gas increases the pressure of the gas. The second pressurized volume of gas may then be released from the pump at a pump outlet. The pump releases the pressurized outlet gas into the airflow path 408 and on towards the exhaust mechanism 414. More details regarding various embodiments of pumps that may provide a sealed positive displacement airflow path are described herein.

The pump 410 may have more than one operating pressure. The pump 410 may operate at various operating pressures while maintaining a similar flow rate through the airflow path 408. For example, the pump 410 may operate at a first operating pressure resulting in a first flow rate of gas through the airflow path 408. The pump 410 may also operate at a second operating pressure resulting in a second flow rate. The first and second flow rates of gas through the airflow path 408 may be the same or substantially similar regardless of the difference in the first and second operating pressures of the pump 410. For example, if blockage or clogging occurs in the airflow path 408, causing a higher pressure within the path 408, the pump 410 may operate at that higher pressure while still maintaining a constant flow rate of air/gas through the airflow path 408.

The terms "pump" and "sealed positive displacement pump" as used herein may refer to mechanisms that may transfer or cause movement of a gas by mechanical action and substantially increase the pressure of that gas as the gas is moved. For instance, as used herein, a pump may refer to any number of different blowers or compressors. Fans, on the other hand, are not considered "pumps" for purposes of this disclosure. Fans may only operate at a pressure ratio of about 1:1. This pressure ratio does not provide a substantial increase in pressure of the gas being moved.

Figures 3, 4:
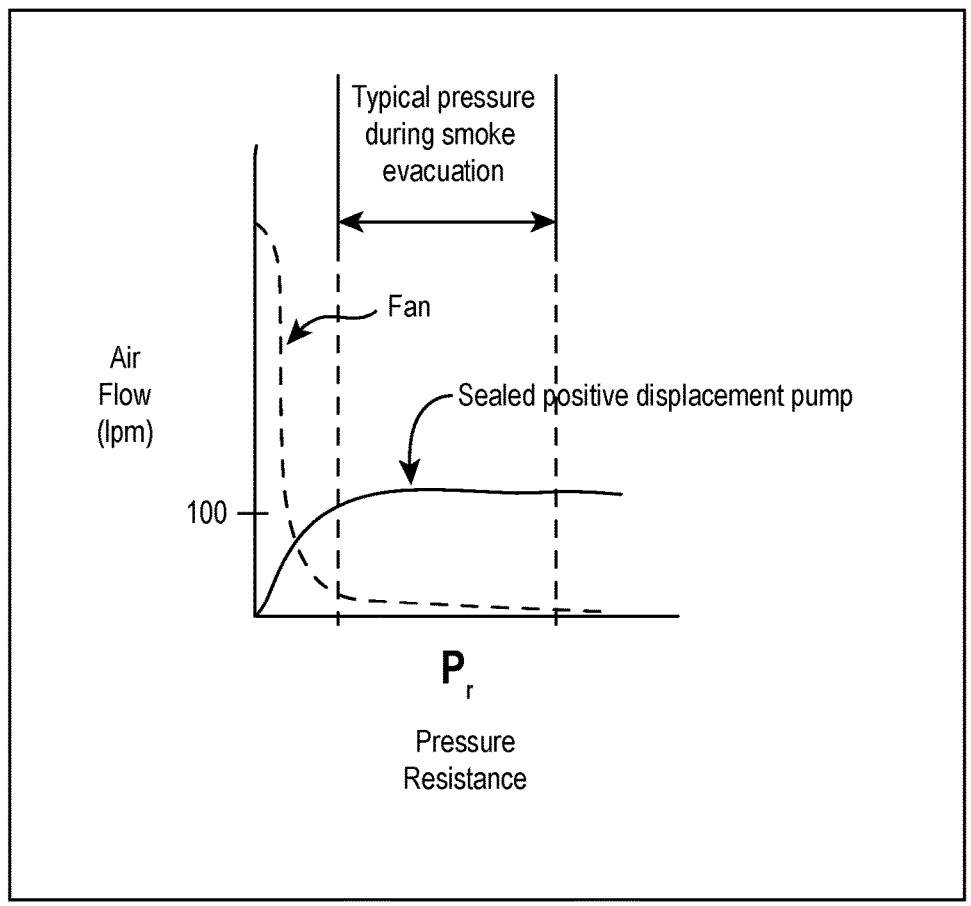
FIG. 3 illustrates resistance pressure vs. air flow for a sealed positive displacement pump and a fan.
FIG. 4 illustrates a table comparing various specifications of a fan, blower, and compressor.

Fans and pumps differ in many respects. A fan may include rotating blades that create a current or flow of gas from one side of the fan to the other. Fans typically operate at a pressure ratio of about 1:1 and move a relatively high volume of air. Typical fans used in smoke evacuation systems may have an operational pressure between atmospheric pressure to about 1.5 psig. The volumetric airflow capacity of a fan decreases dramatically when blockages increase a pressure resistance inside the airflow path 408, as shown in FIG. 3. A sealed positive displacement pump, as described above, is affected less by such blockages and performs well against high resistance pressures, as seen in FIG. 3.

Fans may create suction that draws air through the smoke evacuation system, but they are typically very noisy. The noise can be distracting to practitioners performing surgery. Fans used in typical systems can create sufficient suction but struggle to maintain consistent suction when resistance pressures increase in the system due to airflow obstructions or clogging. Fans are prone to create weak and inconsistent airflow rates through the system.

Blowers differ from fans in that they operate at a higher pressure ratio (e.g., between about 1:1 to 1:2). Essentially, a blower is a high-speed and/or high-volume fan. For example, a blower may be a centrifugal fan that uses rotating impellers to increase the speed and volume of a gas passing through it. Blowers typically have an operational pressure between 1.5 and 1.72 psig and transfer a very high volume of gas relative to fans and compressors.

Compressors are pumps that move relatively low volumes of gas with much higher pressure ratios than fans and blowers. A typical pressure ratio for a compressor, such as those described in various embodiments herein, may be greater than about 2:1. Compressors may operate at a pressure of greater than about 2.72 psig. The various compressors described herein, particularly embodiments that include positive displacement compressors, may be advantageous for a number of reasons. Positive displacement pumps may be much quieter than typical fans used in smoke evacuation systems. Positive displacement pumps also operate well against resistance pressures due to blockages in the airflow path 408 of the smoke evacuation system 400.

Blockages may include unwanted particulate build-up or other clogging due to objects from the ambient air being sucked into the airflow path 408. FIG. 3 illustrates the relationship between pressure resistance and airflow for a positive displacement pump vs. a typical fan. As shown, a sealed positive displacement pump may maintain a relatively steady airflow regardless of the pressure resistance in the system due to clogging. In contrast, the airflow capability of a fan decreases dramatically as the pressure resistance rises. In practice, this indicates that sealed positive displacement pumps, such as the various embodiments described herein, may still create a suction through the smoke evacuation system 400 even when the system clogs or becomes blocked. This is typically not the case if a fan is used.

FIG. 4 is a table showing the pressure increase, operational pressure, pressure ratio, and air volume transferred by a fan, blower, and compressor for comparison. As shown, compressors are able to produce a pressure ratio of greater than 2:1 between a low-pressure gas entering the pump 410 from a first zone 416 of the airflow path 408 and a pressurized gas exiting the pump 410 into a second zone 418 of the airflow path 408.

FIG. 4 also shows the relative air volume moved by the fans, blowers, and compressors. Compressors move the lowest volume of air relative to fans and blowers, and fans move the highest volume of air when air flow path conditions are equivalent. FIG. 4 also shows that compressors operate at a pressure ratio of greater than 2:1, as opposed to fans and blowers that operate at pressure ratios closer to 1:1. This means that air/gas exiting a compressor is typically pressurized at twice the pressure of the air/gas entering the compressor at a compressor inlet.

The various embodiments of the smoke evacuation system, as described herein, may include one or more various types of pumps. The various pumps may be incorporated into the system in order to reduce noise and vibrations, which can be irritating to users and damaging to the system. For example, typical fans used in current systems may be very noisy and cause significant vibrations. These vibrations can cause the system to travel along a surface where it is placed, thus requiring a secure connection to that surface. This secure connection diminishes the portability of the system and increases the difficulty of installation. Vibrations can also be damaging to internal components of the system, which may not be designed to withstand such vibrations.

The following description includes various embodiments of a smoke evacuation system, including various types of pumps, vibration absorption mechanisms, and motor control methods aimed at reducing the noise and vibration of the system in order to solve these problems.

Figure 5A:
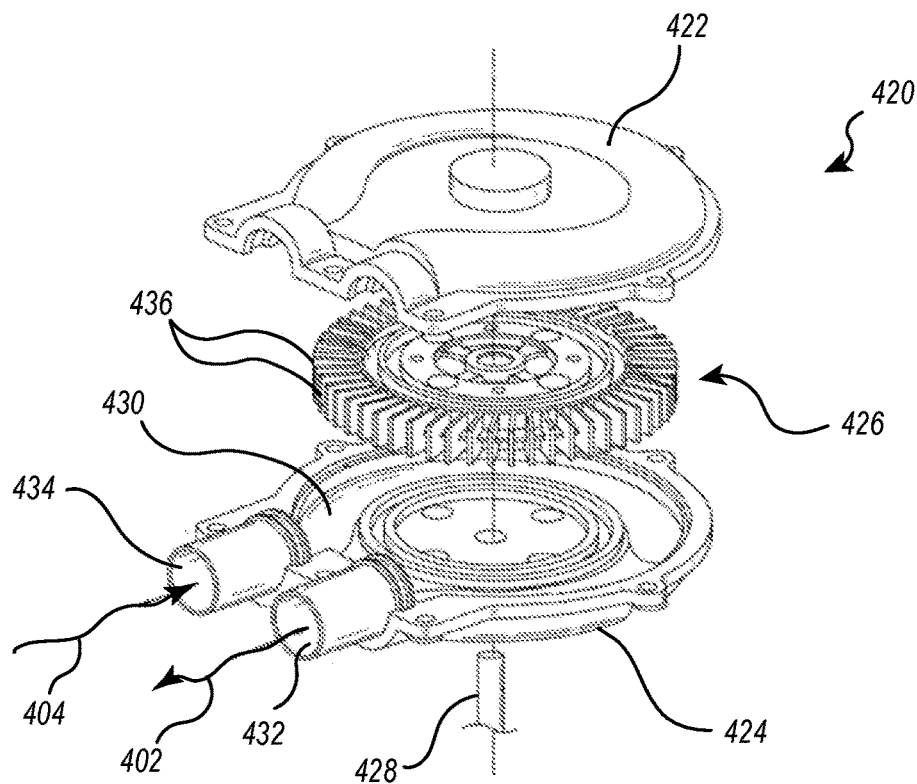
FIG. 5A illustrates an exploded view of a hybrid regenerative blower.
Figure 5B:
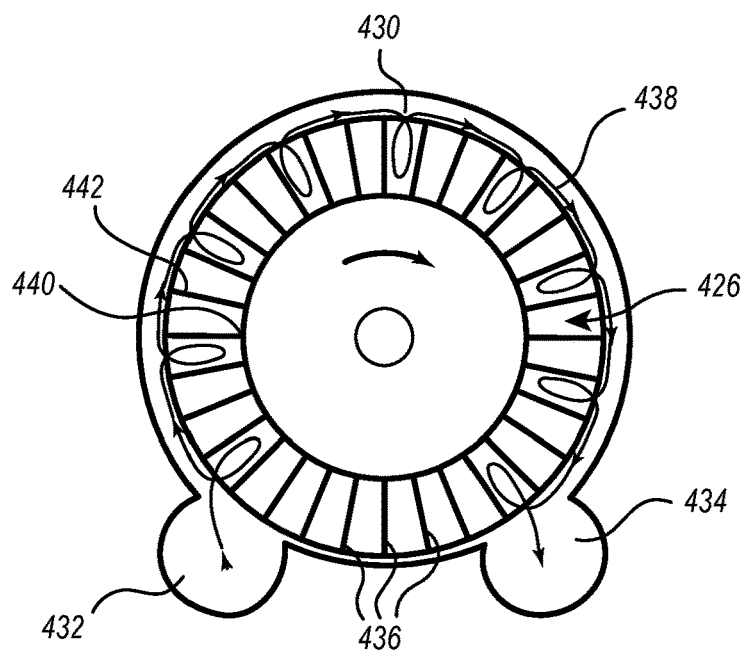
FIG. 5B illustrates a cross-sectional view of the hybrid regenerative blower illustrated in FIG. 5A.

In one embodiment of a smoke evacuation system 400, the pump 410 shown in FIG. 2 may be a blower 420, as illustrated in FIGS. 5A-5B. FIG. 5A illustrates an exploded view of blower 420. The blower 420 may be a hybrid regenerative blower with impeller features that compress the gas 402 passing there through. The blower 420 may include a top cover 422, a bottom cover 424, and an impeller assembly 426. A rotary shaft 428 may be secured to the center of the impeller assembly 426 and cause the impeller assembly 426 to rotate. A motor 412 that may engage the rotary shaft 428 is not illustrated in FIG. 5A, but is shown in FIG. 2.

The top cover 422 may be secured to the bottom cover 424 to create a sealed circulation path 430 having an inlet 432 and an outlet 434. The circulation path 430 may also be referred to as an airflow path 430 of the blower. The impeller assembly 426 may be disposed between the top cover 422 and bottom cover 424 so that the impeller blades 436 reside within the sealed circulation path 430. A motor drives the impeller assembly 426 to rotate about the rotary shaft 428 so that the impeller blades 436 travel in a circular path through the sealed circulation path 430. This circular motion of the impeller blades 436 creates a suction so that a gas 402 is drawn into the inlet 432, travels around the sealed circulation path 430, and exits the blower 420 out of the outlet 434.

FIG. 5B illustrates the flow path 438 of a gas 402 flowing through the sealed circulation path 430 of the blower 420. FIG. 5B illustrates a cross-sectional view of the blower 420 showing impeller assembly 426 inside sealed circulation path 430. The impeller assembly 426 is driven clockwise in this embodiment. As the impeller blades 436 rotate through the sealed circulation path 430, centrifugal force moves gas molecules from the blade root 440 to its tip 442. The gas molecules then leave the blade tip 442 and enter the portion of the sealed circulation path 430 not occupied by the impeller blades 436. The gas molecules are then drawn back down a succeeding impeller blade 436 in repeated fashion.

This repeated flow path 438 of the gas provides a quasi-staging effect that may increase a pressure differential capability of the blower 420. This type of regenerative blower 420 passes the gas through many compression cycles as the gas molecules pass up and down various impeller blades 436 with each revolution of the impeller assembly 426. Thus, a gas exiting the outlet 434 may have a higher pressure than the gas entering at the inlet 432. The speed of the rotating impeller assembly 426 is proportional to the pressure differential of the gas. For example, a higher rotational speed of the impeller assembly 426 increases the pressure differential between the gas at the inlet 432 compared to the gas exiting at the outlet 434. A lower rotational speed results in a lower pressure differential.

The number of impeller blades 436 may be odd so as to limit resonance, which can create noise and vibrations. An odd number of blades 436 reduces the chance of elastic frequencies from the blades 436 becoming tuned to a resonant frequency of the rotary shaft 428. Natural frequencies of the top and bottom covers 422, 424 are also offset from the frequencies of the blades 436 and rotary shaft 428 to limit noise and vibrations of the blower 420 due to the harmonics of the blower 420.

Figure 6A:
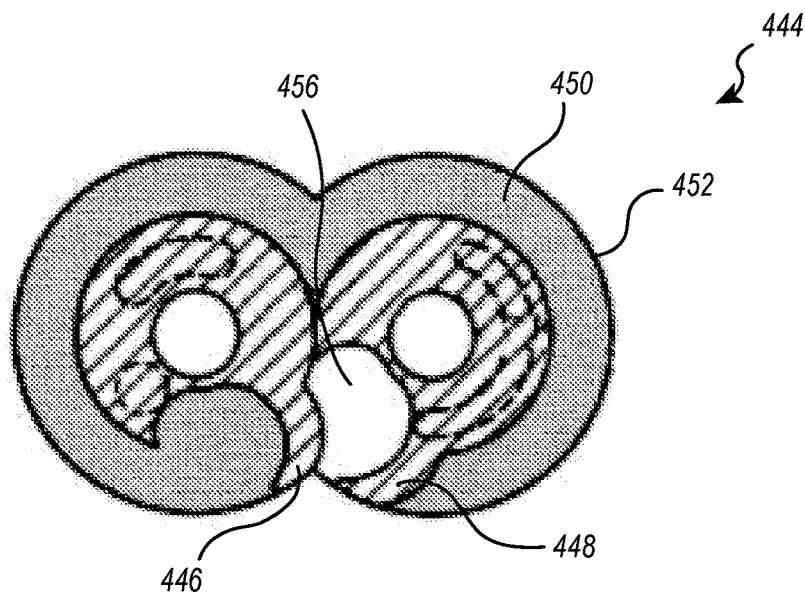
FIGS. 6A through 6C illustrate cross-sectional views of various stages of a claw pump.
Figure 6B:
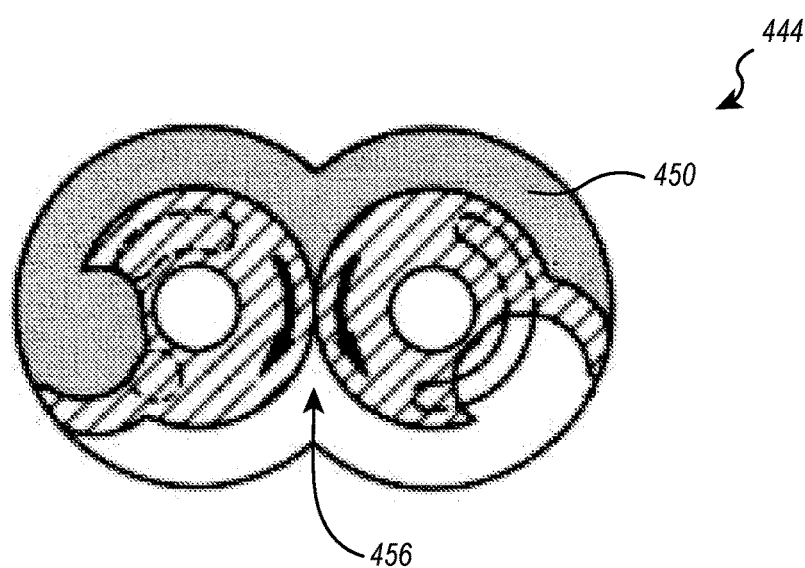
Figure 6C:
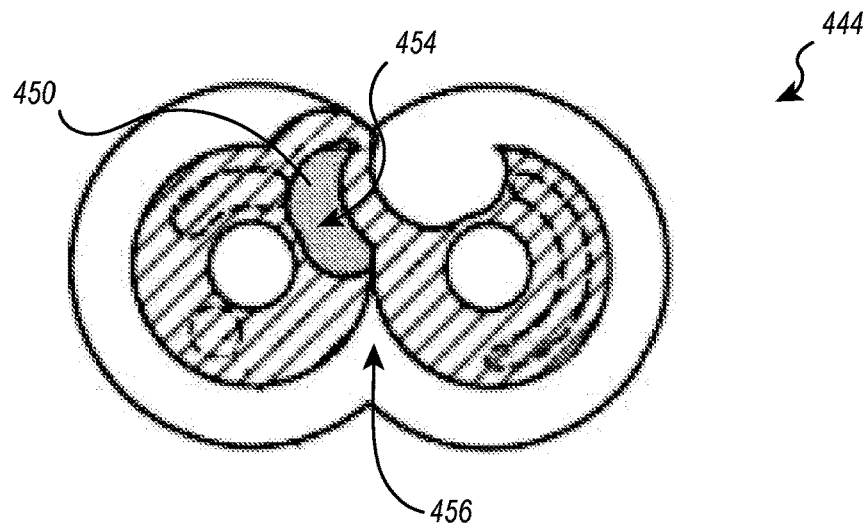

In one embodiment of a smoke evacuation system 400, the pump 410 shown in FIG. 2 may be a claw pump 444. Various cross-sectional views of the claw pump 444 are illustrated in FIGS. 6A-6C. The claw pump 444 may be a cooperative dual drive shaft claw pump. FIGS. 6A-6C illustrate a top cross-sectional view of the claw pump 444 in three different stages of rotation. The claw pump 444 is a positive displacement pump that compresses gas by decreasing the volume of an initial volume of gas that enters the pump.

The claw pump 444 may have first and second counter-rotating rotary elements, or claws 446, 448 disposed within a single circulation path of the pump 444. For example, the first claw 446 may rotate clockwise and the second claw 448 may rotate counter-clockwise, as indicated by the arrows in FIG. 6B. FIG. 6A shows an initial state of the claw pump 444 where a gas 450 resides in a sealed space between the claws 446, 448 and the pump housing 452. The gas 450 is illustrated in gray. As the claws 446, 448 rotate, the volume of the sealed space in which the gas 450 resides decreases due to the geometry of the claws 446, 448. FIG. 6C illustrates the gas 450 in a compressed state, where the volume of the sealed space in which the gas 450 resides has been reduced due to the rotation of the claws 446, 448.

Decreasing the volume of the gas 450 pressurizes the gas. The inlet and outlet ports of the claw pump 444 are not shown in detail because of the top cross-sectional view of FIGS. 6A-6C. An inlet 456 may, for example, be disposed below the claw pump 450 an outlet 454 may be disposed above the claw pump 444 so that the compressed volume of gas 450 shown in FIG. 6C may enter and exit via the inlet 456 and outlet 454 perpendicular to the viewing plane. In other words, the inlet 456 and outlet 454 may be configured so that the inlet 456 is disposed below the viewing plane and the outlet 454 is disposed above the viewing plane, or vice versa, so that the gas travels through the claw pump 444 perpendicular to the viewing plane.

Embodiments of the smoke evacuation system 400 that may include a cooperative dual drive shaft claw pump 444 such as the one illustrated in FIGS. 6A-C may enjoy reduced noise and vibrations. Pumps with single shaft rotary elements may suffer from vibrations due to slight imbalances of components that rotate around a central drive shaft. In the cooperative dual drive shaft claw pump 444 illustrated, the two rotating claws 446, 448 rotate in opposite directions and may balance each other out. This balance may minimize vibrations.

Figure 7A:
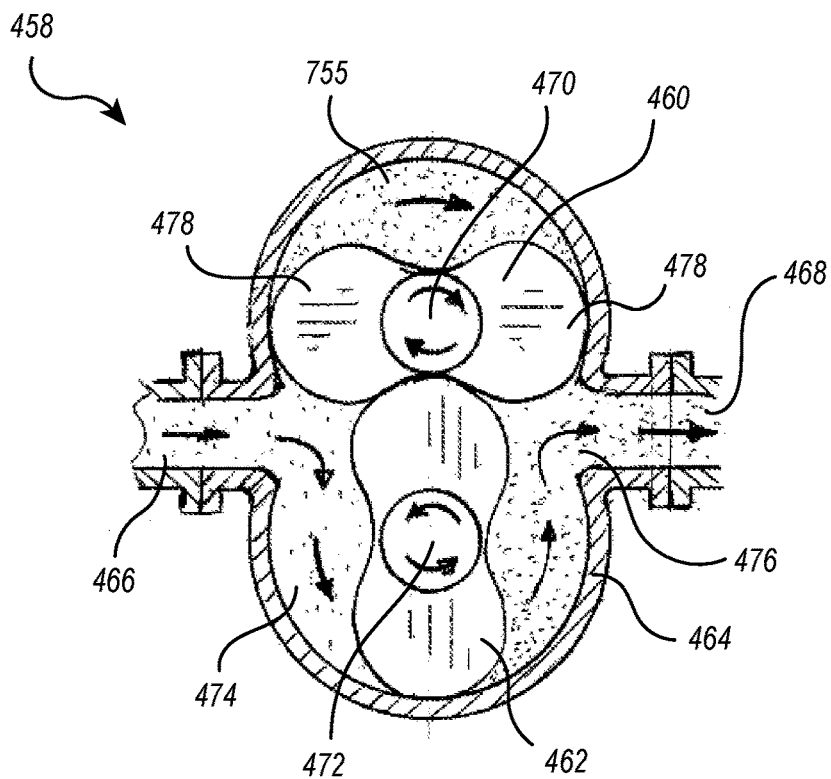
FIG. 7A illustrates one embodiment of a lobe compressor having two lobes.

In one embodiment, the pump 410 of the smoke evacuation system 400 may also be a lobe compressor 458. FIG. 7A illustrates a cross-sectional view of a lobe compressor 458 including two counter-rotating rotary elements 460, 462. Each rotary element 460, 462 may have two or more lobes 478. The lobe compressor 700 functions similarly to the claw pump 444 described herein, in that the two rotary elements 460, 462 rotate in opposite directions, as indicated by the arrows marked on the two rotary shafts 470, 472, in order to create a sealed positive displacement airflow path through the compressor 458.

The rotation of the rotary elements 460, 462 draws in a low-pressure gas 474 through an inlet 466 and moves the gas 474 through the compressor 458 to an outlet 468. As the gas 474 moves through the compressor 458, as indicated by the arrows, the volume of the gas 474 decreases, which pressurizes the gas. The pressurized gas 476 then exits the compressor 458 via the outlet 468.

Figure 7B:
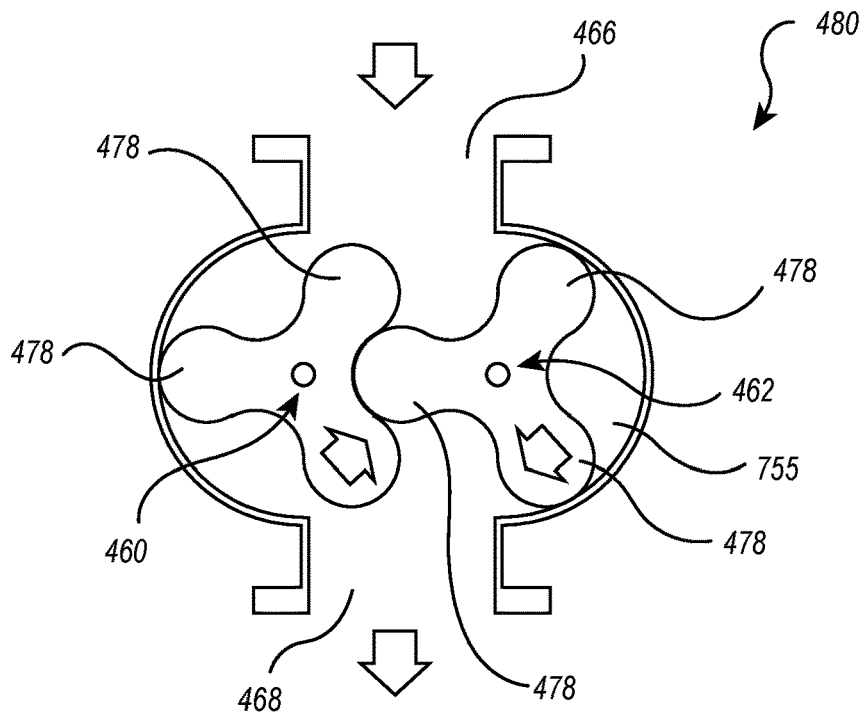
FIG. 7B illustrates one embodiment of a lobe compressor having three lobes.

Other embodiments of the smoke evacuation system 400 may include lobe compressors 700 having more than two lobes 478 on each rotary element 460, 462. For example, FIG. 7B illustrates a lobe compressor 480 that comprises two rotary elements 460, 462 having three lobes 478 each. In this embodiment, a low-pressure gas is drawn into the inlet 466, driven through the compressor 480 via the rotating lobes 478, after which the volume of the inlet gas is reduced and pressurized before it exits out the outlet 468 of the compressor 480.

Figure 7C:
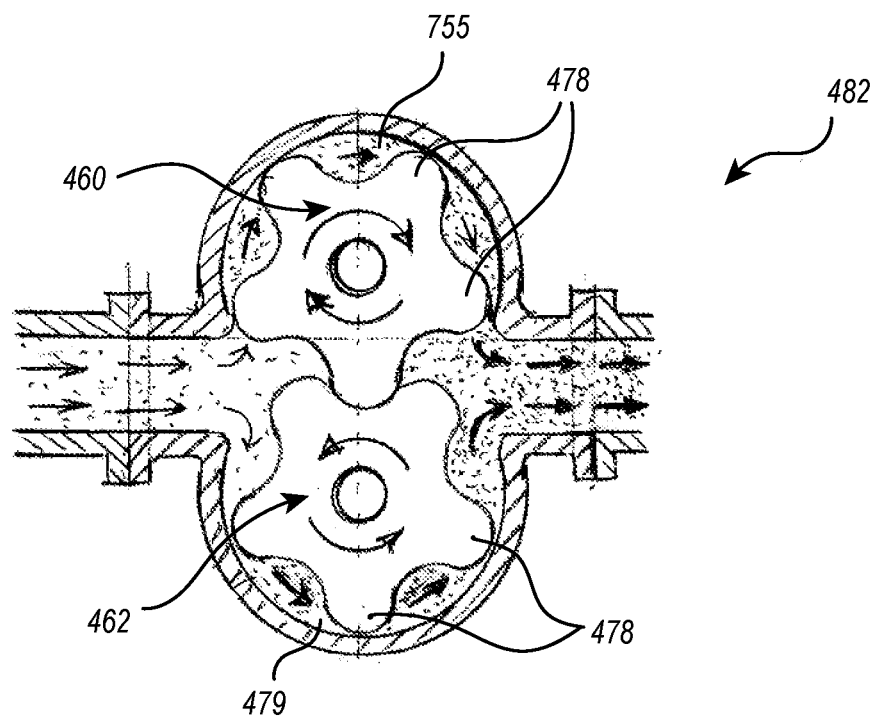
FIG. 7C illustrates one embodiment of a lobe compressor having five lobes.

FIG. 7C illustrates yet another embodiment of a lobe compressor 482 that operates similar to the other lobe compressors described herein. The lobe compressor 482 illustrated in FIG. 7C includes two rotary elements 460, 462 that have five lobes each. Other embodiments may include lobe compressors with rotary elements that have four lobes, or more than five lobes.

In the various embodiments of lobe compressors illustrated in FIGS. 7A-7C, the two rotary elements maintain consistent contact with each other while rotating. For instance, each lobe 478 of one rotary element extends between two lobes of the other rotary element so that contact is maintained as the rotary elements rotate. Thus, air may not escape from between the lobes. Instead, the air is trapped within sealed compartments as the air moves through the lobe compressors.

Other embodiments of a smoke evacuation system 400 may include multiple rotary elements that cooperatively counter-rotate to produce a sealed circulation path that traps and compresses gas by positive displacement action. These other pumps may include, but are not limited to, two stage rotary vane pumps and dual screw eccentric pumps. The various counter rotating dual drive shaft pumps with multiple rotary elements described herein may provide a pressure differential of at least 1.5 psig between a low-pressure inlet gas entering the pump 410 from a first zone 416 of the airflow path 408 and a high-pressure outlet gas exiting the pump 410 into a second zone 418 of the airflow path 408. Other embodiments may include similar pumps that produce a pressure differential of between 1 and 2 psig. Yet other embodiments may produce a pressure differential of greater than 2 psig.

The various counter rotating dual drive shaft pumps with multiple rotary elements may also reduce vibration and noise within the smoke evacuation system 400 for the same reasons as discussed above in reference to the claw pump 444. The two rotary elements rotate in opposite directions and balance each other out. This balance may cancel out vibrations and resulting noise.

In one embodiment of the smoke evacuation system 400, the pump 410 may be a scroll compressor. Scroll compressors are positive displacement compressors. The various embodiments of a scroll compressor described herein may achieve all the advantages of the pumps described above, including but not limited to the same compression ratios, operating pressures, vibration reduction, and noise reduction of the smoke evacuation system 400.

Figure 8:
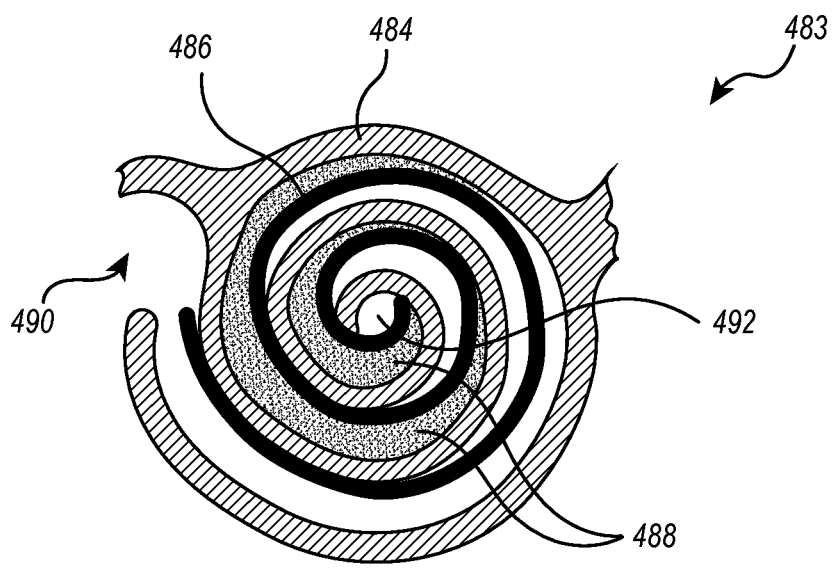
FIG. 8 illustrates a cross-sectional view of on embodiment of a scroll compressor.

FIG. 8 illustrates a cross-sectional view of a scroll compressor 800. The scroll compressor may include a stator scroll 484 and a moving scroll 486. The stator scroll 484 is fixed in position while the moving scroll 486 orbits eccentrically without rotating. The moving scroll 486 may orbit eccentrically such that the moving scroll 486 does not rotate about its own central longitudinal axis, but the central longitudinal axis of the moving scroll 486 would orbit about a central longitudinal axis of the stator scroll 484. The central longitudinal axes of the stator and moving scrolls 484, 486 extend perpendicular to the viewing plane of the scrolls 484, 486. The stator scroll 484 and the moving scroll 486 may be interleaved with each other to form discreet sealed compression chambers 488.

A gas may enter the scroll compressor 483 at an inlet 490. As the moving scroll 486 orbits, the inlet gas is first trapped in a compression chamber 488. The compression chamber 488 moves a discreet volume of gas along the spiral contour of the scrolls 484, 486 toward the center of the scroll compressor 483. The compression chamber 488, or sealed space in which the gas resides, decreases in volume as the gas moves toward the center of the stator scroll 484. This decrease in volume increases the pressure of the gas inside the compression chamber 488. The gas inside the sealed compression chamber 488 is trapped while the volume decreases, thus pressurizing the gas. Once the pressurized gas reaches the center of the scroll compressor 483 it is released through an outlet 492.

Figure 9:
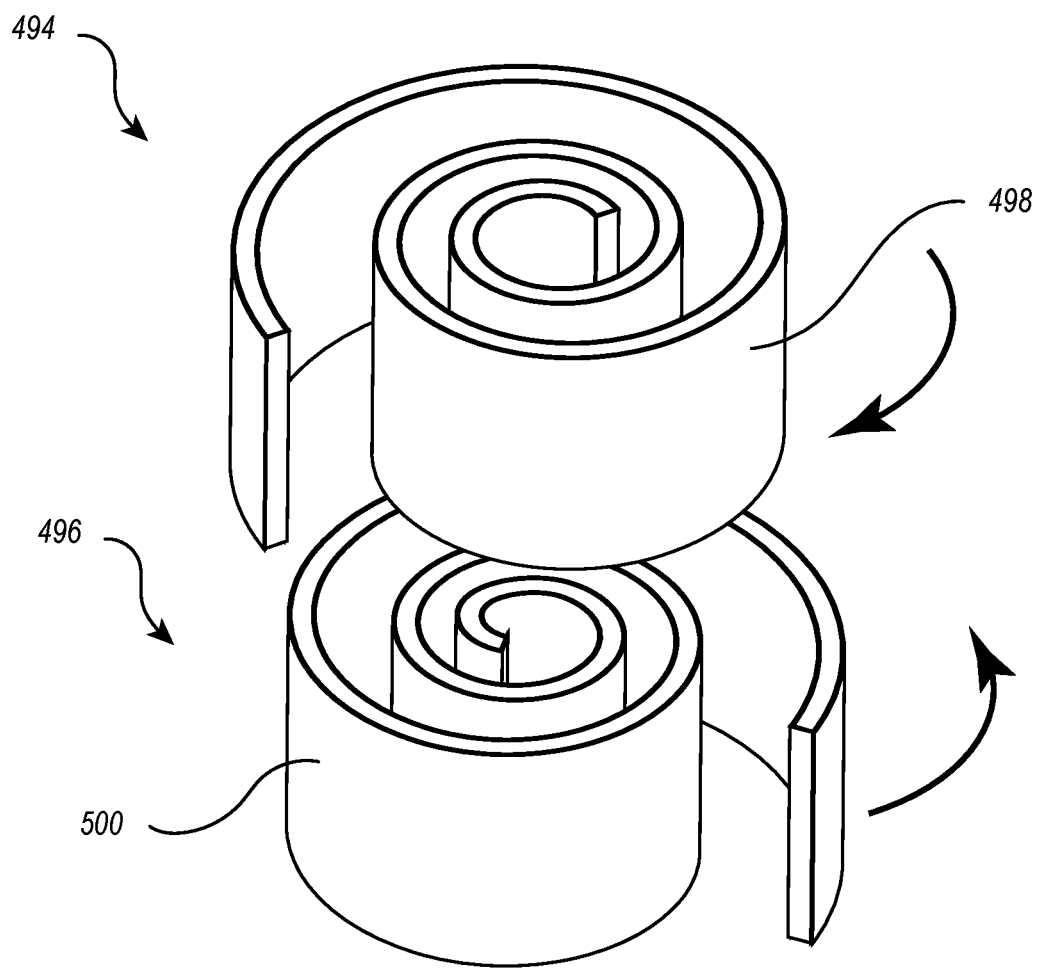
FIG. 9 illustrates one embodiment of a dual, in-line scroll compressor.

Two or more scroll compressors may be disposed in series in order to counterbalance vibrations that may be caused by the orbiting of the moving scroll 486. FIG. 9 illustrates a perspective view of two scroll compressors 494, 496 disposed in series. Only the moving scrolls 498, 500 are shown for illustrative purposes. The first moving scroll 498 may be oriented at 180-degrees from the second moving scroll 500. The first moving scroll 498 of the first scroll pump 494 may orbit in an opposite direction of the second moving scroll 500 of the second scroll pump 496. For example, the first moving scroll 498 may orbit counterclockwise and the second moving scroll 500 may orbit clockwise. Other embodiments may include first and second scroll pumps 494, 496 that are oriented opposite of the scrolls illustrated.

The two scroll pumps 494, 496 may be disposed in series within a sealed airflow path 408. In such a configuration, compressed gas exiting the first scroll pump 494 at an outlet of the first scroll pump 494 may enter an inlet of the second scroll pump 496 to be further compressed. A single scroll pump, such as those described above, orbits eccentrically and therefore inherently shifts its weight around while orbiting to produce vibrations. The opposite orbiting movement of the two scrolls 498, 500 in series, illustrated in FIG. 9, may counterbalance one another in order to limit vibrations in the system 400.

Alternatively, another dual scroll pump embodiment may include two scroll pumps 494, 496 aligned parallel to one another so that parallel flow paths pass through each scroll pump 494, 496. Each scroll pump 494, 496 may have an inlet from a common airflow path 408 and an outlet communicating with a common airflow path 408. Dual scroll pumps 494, 496 aligned parallel in this manner may provide twice as much airflow through the system 400 than other embodiments described herein.

Figure 10A:
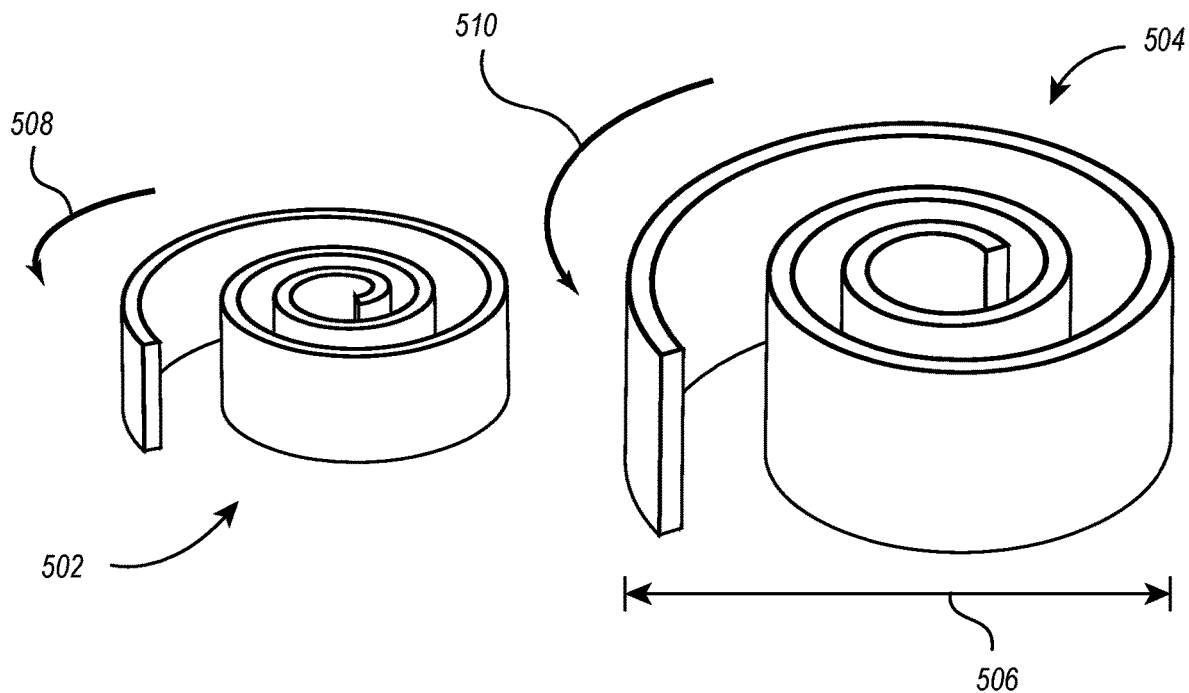
FIG. 10A illustrates one embodiment of a high flow and a low flow scroll.

In one embodiment of the smoke evacuation system 400, the pump 410 may comprise two scroll pumps of different sizes. FIG. 10A illustrates a perspective view of first and second scroll pumps 502, 504. For the sake of simplicity in illustration, stator scrolls of the scroll pumps 502, 504 are not shown. Rather, only the moving scrolls 502, 504 are shown for illustrative purposes. The first scroll 502 may be a low flow-capacity scroll that orbits at a relatively low revolutions-per-minute ("RPM") compared to the other pumps described herein. The second scroll 504 may be a high flow-capacity scroll that also orbits at a relatively low RPM. The high flow scroll 504 may have a higher flow-capacity than the low flow-capacity scroll 502 even when the two are orbiting at the same RPM due to a larger diameter 506 compared to a diameter of the low flow-capacity scroll 502.

The low-flow scroll 502 and the high flow scroll 504 may be disposed in series, as described previously in reference to the dual in-line scroll pump illustrated in FIG. 9. The two scrolls 502, 504 may also be disposed next to each other as illustrated in FIG. 10A. Arrows 508 and 510 indicate the orbiting direction of the low flow and high flow scrolls 502, 504, respectively. FIG. 10A illustrates both scrolls orbiting in a counter-clockwise direction. Other embodiments may include scrolls that orbit clockwise. Yet other embodiments may include scrolls that orbit in opposite directions to one another.

Figure 10B:
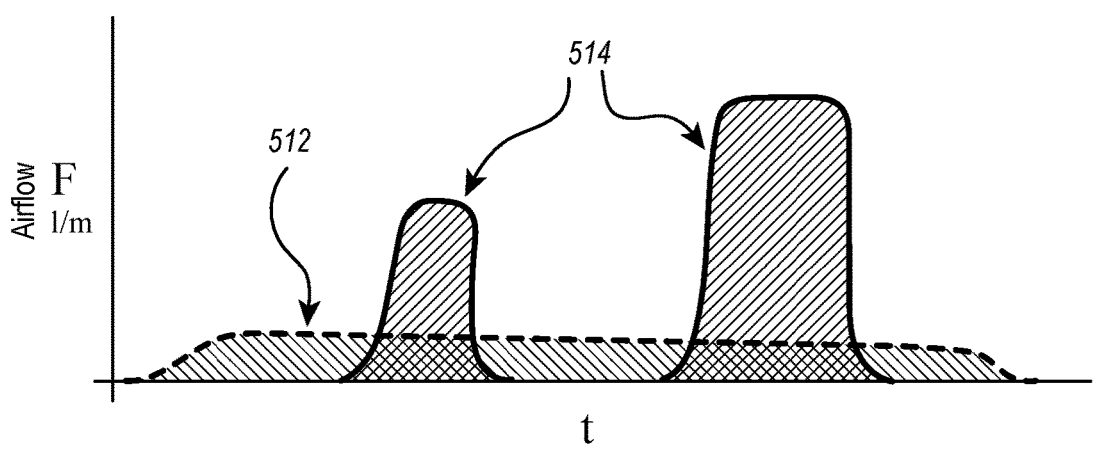
FIG. 10B illustrates the relationship of time vs. airflow for both the low flow scroll and the high flow scroll illustrated in FIG. 10A.

Pairing a low flow scroll 502 with a high flow scroll 504 as described above has a number of advantages. The configuration illustrated in FIG. 10A may allow for variable selectable flow rates without increasing the RPM of the scrolls. For example, as illustrated in FIG. 10B, the low flow scroll 502 may produce a constant low-level airflow 512 over time. The high flow scroll 504 may provide higher flows over time. The high flow scroll 504 may be selectively turned on and off to provide discrete higher flows 514 when needed. Such a need may arise, for example, to overcome a temporarily increased pressure resistance (e.g., due to clogging) within the airflow path 408 of the smoke evacuation system 400.

Thus, variable flow rates can be accomplished while maintaining a low RPM of the orbiting scrolls. Maintaining low RPMs of the scrolls may decrease vibrations and noise of the pump 410.

Vibration Absorption Mechanisms

Components of typical smoke evacuation systems, such as pumps and motors, may create unwanted or even damaging vibrations. Vibrations can damage components of the system or shorten their useful lifespan. Vibrations can even cause components of the system to move across the surfaces on which they rest, requiring that they be fixed to the surface. This decreases the portability of the system and increases the difficulty of installation. Vibration absorption mechanisms may be incorporated into the smoke evacuation system 400 to further limit vibrations. These absorption mechanisms can be used in conjunction with the various pumps described herein, or they may be incorporated separately into various other embodiments of the system 400.

Figure 11:
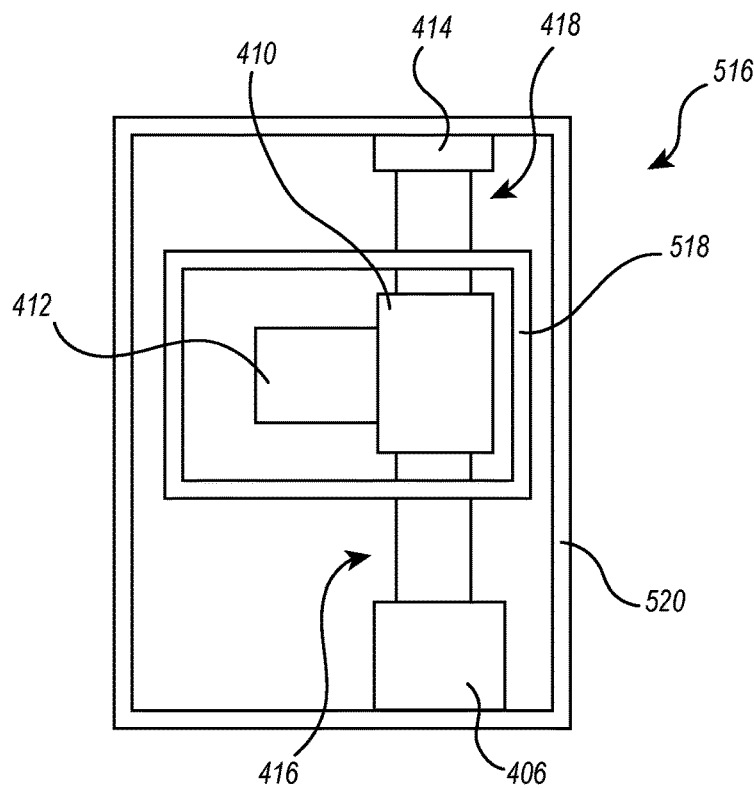
FIG. 11 illustrates an embodiment of a smoke evacuation system including inner and outer housings.

FIG. 11 illustrates in schematic form an embodiment of a smoke evacuation system 516 that includes an inner housing 518 and an outer housing 520. The inner housing 518 may house the motor 412 and pump 410 of the smoke evacuation system 516. In some embodiments, the inner housing 518 may house various other components of the smoke evacuation system 516. For example, the inner housing 518 may house the motor 412, pump 410, and exhaust mechanism 414. Also, for example, the inner housing 518 may only house the pump 410 or the motor 412. In the illustrated embodiment of FIG. 11, the inner housing 518 also includes portions of the first zone 416 and second zone 418 of the airflow path 408 (See FIG. 2).

The first zone 416 of the airflow path 408 may be an inlet to the pump 410 that may pass through the inner housing 518. Likewise, the second zone 418 of the airflow path 408 may be an outlet from the pump that may pass through the inner housing 518 as well. Other embodiments of a smoke evacuation system may include an inner housing 518 that houses all or none of the first and second zones 416, 418 of the airflow path 408.

FIG. 11 illustrates a cross-sectional view of smoke evacuation system 516 in order to show the configurations of the inner and outer housings 518, 520. In some embodiments, the inner housing 518 may completely encapsulate various components of the system 516, such as the pump 410 and the motor 412, thus totally isolating them from other components of the system 516, such as the filter 406 and exhaust mechanism 414. In other embodiments, the inner housing 518 may only partially surround or encapsulate these or other components.

The outer housing 520 may house other components of the smoke evacuation system 516 that are not housed within the inner housing 518. For example, the embodiment illustrated in FIG. 11 shows outer housing 520 that houses the filter 406, exhaust mechanism 414, and portions of the first and second zones 416, 418 of the airflow path 408. The outer housing 520 may also house the entire system, including the inner housing 518 and components therein.

FIG. 11 illustrates a cross-sectional view of a smoke evacuation system 516 in order to show the configurations of the inner and outer housings 518, 520. In some embodiments, the outer housing 520 may completely encapsulate various components of the system 516, such as the filter 406 and the exhaust mechanism 414, thus totally isolating them from an exterior environment surrounding the system 516. The outer housing 520 may also encapsulate the inner housing 518. The outer housing 520 may completely encapsulate components of the smoke evacuation system 516 not encapsulated by the inner housing 518, such as the filter 406 and exhaust mechanism 414. In other embodiments, the outer housing 520 may only partially surround or encapsulate these or other components.

Figure 12:
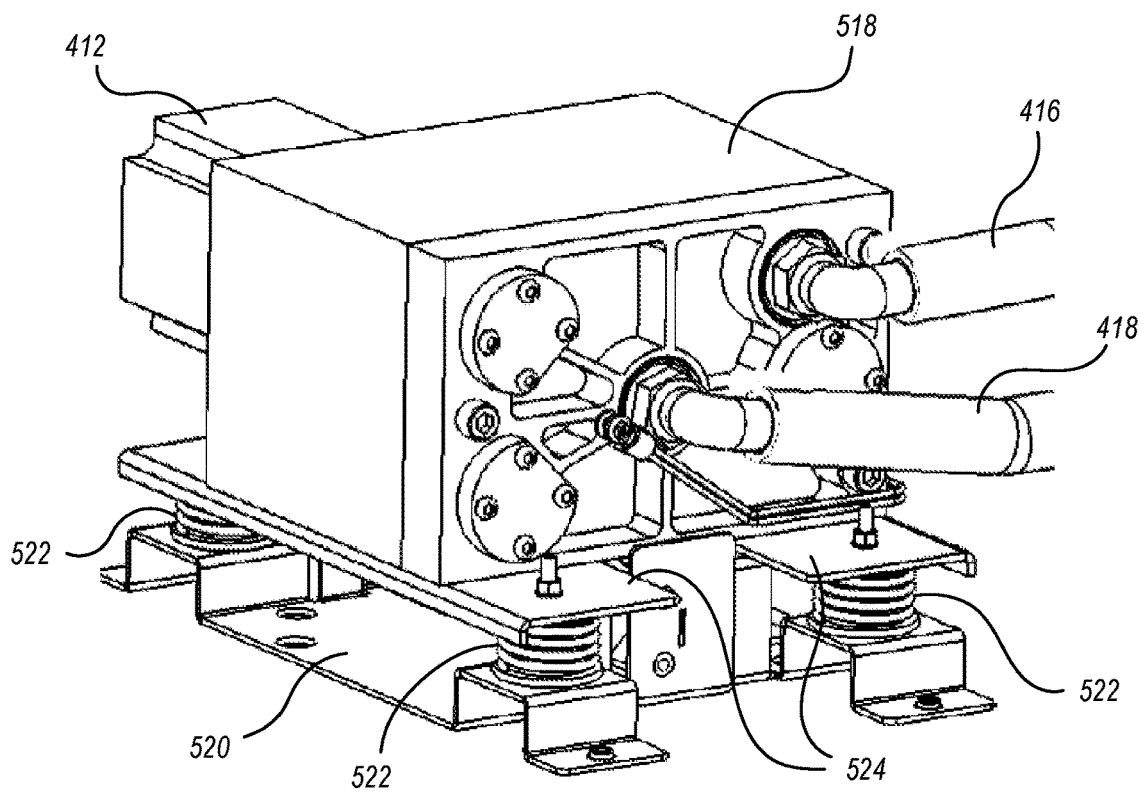
FIG. 12 illustrates on embodiment of vibration absorption mechanisms disposed between inner and outer housings.

Vibration absorption mechanisms may be disposed, and serve as interfaces, between the inner and outer housings 518, 520. FIG. 12 illustrates an inner housing 518 interfacing with an outer housing 520 via various vibration absorption mechanisms 522. Only a portion of the outer housing 520 is shown for illustrative purposes. Various components of a smoke evacuation system 400 are also shown, including first and second zones 416, 418 of the airflow path 408, which may serve as an inlet and outlet of the pump disposed within inner housing 518. The filter 406 (illustrated in FIG. 11), motor 412, and first and second zones 416, 418 of the airflow path 408 may be disposed within the outer housing 520 but outside the inner housing 518. The pump 410 may be enclosed inside the inner housing 518 and therefore not shown in FIG. 12.

In the embodiment illustrated in FIG. 12, vibration absorption mechanisms 522 may comprise springs disposed between inner and outer housings 518, 520. The pump and/or motor enclosed/housed within the inner housing 518 may create vibrations that result in unwanted movement or noise of the system. The vibration absorption mechanisms 522 may absorb these vibrations so that a substantial portion of the vibrations are not transferred to the outer housing 520.

For example, the springs 522 illustrated in FIG. 12 may compress, stretch, or laterally flex due to vertical or horizontal vibrational forces acting on the springs 522. These forces may be a result of the inner housing 518 vibrating up and down, or laterally. These movements caused by the vibrating motor and/or pump within the inner housing 518 may be transferred into the springs 522. As the springs 522 compress, stretch, or laterally flex, the spring may absorb a substantial portion of the vibrations. Thus, the vibrations may not be substantially transferred from the inner housing 518 to the outer housing 520.

FIG. 12 illustrates an embodiment wherein four vibration absorption mechanisms 522 are disposed between the inner housing 518 and the outer housing 520. Other embodiments may include more or less than four vibration absorption mechanisms 522 disposed between the inner housing 518 and the outer housing 520. The location of the vibration absorption mechanisms 522 may also vary in other embodiments. For example, a vibration absorption mechanism 522 may be disposed at the bottom center of the inner housing 518, rather than just at the bottom four corners of the inner housing 518 as illustrated.

In the embodiment illustrated in FIG. 12, a number of plates 524 may be secured to or integrally formed with the inner housing 518 and the vibration absorption mechanisms 522 may be secured directly or indirectly to the plates 524. Other embodiments may or may not include plates 524. For example, other embodiments may have vibration absorption mechanisms 522 that are secured directly to the inner housing 518. Other embodiments may include more or less than two plates 524 secured to both the inner housing 518 and vibration absorption mechanism 522 as illustrated in FIG. 12.

FIG. 13A shows an inner housing 518 secured to an outer housing 520 via plates 524 and vibration absorption mechanisms 526. The vibration absorption mechanisms 526 of the embodiment illustrated in FIG. 13A may be ring isolators 526. Similar to the springs 522 disposed between the plates 524 and outer housing 520 illustrated in FIG. 12, the ring isolators 526 may absorb vibrations from the pump 410 and/or motor 412 housed within the inner housing 518 so that a substantial portion of those vibrations are not transferred to the outer housing 520.

FIG. 13B illustrates how the ring isolators 526 may be secured to the housings 518, 520 and/or plates 524. The ring isolators 526 may be configured in a circular ring shape and be disposed between the plate 524 and outer housing 520 so that the ring isolator 526 acts as a barrier between the two, as illustrated in FIGS. 13B and 13C. Two or more securing mechanisms 528 may secure the plate 524 and outer housing 520 to the ring isolator 526 on opposing sides of the ring isolator 526 as shown. The securing mechanisms 528 illustrated in FIGS. 13B and 13C comprise a nut and bolt assembly. Other embodiments may include other securing mechanisms 528. For example, other embodiments may include securing mechanisms 528 that comprise nails, screws, adhesives, clips, hooks, and the like.

FIG. 13C illustrates how a ring isolator 526 may absorb vibrations. The ring isolator may be comprised of a flexible material such as an elastomer. For example, one embodiment of the ring isolator 526 may be made of silicone. Other embodiments may include ring isolators 526 that comprise other elastomeric materials, such as rubber. The ring isolator 526 may flex when acted upon by a force, such as the forces created by vibrations 530. FIG. 13C illustrates vibrations 530 pushing down on the plate 524. These vibrations 530 push down on the plate 524, which pushes down on the ring isolator 526, which may cause the ring isolator 526 to flex in such a way so as to compress the ring isolator 526. The compressed ring isolator 526 may absorb the movement of the plate 524 due to the vibrations 530 without transferring a substantial portion of that movement into the outer housing 520.

Vibrations 530 may be oscillatory movements that create forces that may push downward, pull upward, or pull sideways on the plate 524. As will be appreciated, the ring isolator 526 may absorb all of these potential movements of the plate 524 by deforming and/or flexing in all different directions. For example, the ring isolator 526 may expand and stretch taller, or shift side to side in response to various vibrational forces. In this way, ring isolators 526 may absorb the vibrations 530 of the inner housing 518 so the vibrations 530 are not substantially transferred to the outer housing 520.

FIG. 14A illustrates an embodiment where the vibration absorption mechanism comprises an elastomeric sheet 532. The elastomeric sheet 532 may be disposed between the plates 524 and outer housing 520 similar to the springs 522 and ring isolators 526 described herein. The elastomeric sheet 532 may be a single sheet covering an entire area between the first housing 518 and the second housing 520 as shown in FIG. 14A. Other embodiments may include multiple sheets 532. For example, in one embodiment, the sheet 532 may comprise four separate sections disposed at the four bottom corners of the inner housing 518 and/or plates 524, similar to where the ring isolators 526 are disposed according the embodiment illustrated in FIG. 13A. Other embodiments may include two separate sheets 532, each connecting two corners of the inner housing 518 and/or plates 524 to the outer housing 520.

FIG. 14B shows one way in which the elastomeric sheet 532 may be secured between the plate 524 and the outer housing 520. In the illustrated embodiment, two nuts molded into the sheet 532 provide a fixture through which two screws/bolts may be threaded from above the plate 524 and below the outer housing 520. Other embodiments may include other securing mechanisms, such as nails, hooks, adhesives, and so forth. Once secured, the sheet 532 may absorb vibrations from the inner housing 518 due to the pump 410 or motor 412 and substantially prevent those vibrations from being transferred to the outer housing 520.

In addition to the various vibration absorption mechanisms described herein, additional vibration absorption mechanisms may be employed in conjunction with those described in other embodiments. FIG. 15 shows a tube configuration that may enhance the vibration absorption capabilities of various tubes. More specifically, FIG. 15 shows bent tubes 536, 537 that may absorb vibrations due to their bent configuration. The tubes 536, 537 may be inlet and/or outlet tubes to the pump 410 residing within the inner housing 518. The motor 412 may be disposed outside the inner housing 518 and engage the pump 410 through the housing 518. The motor 412 and/or pump 412 may create vibrations in the system that may travel into the inner housing 518 and through the tubes 536, 537.

The tubes 536, 537 may include a U-shaped portion 538 at one or more locations along the length of the tubes 536, 537. The U-shaped portions 538 of the tubes 536, 537 may allow the tubes 536, 537 to flex in response to vibrations to a greater degree than straight tubes having no U-shaped portions 538. The U-shaped portions 538 of the tubes 537 also may increase the total length of the tubes 536, 537 to increase the amount of tube material available to absorb and dampen vibrations. In the embodiment shown in FIG. 15, each tube 536, 537 has one U-shaped portion 538. Other embodiments may include more than one U-shaped portion 538. Some embodiments may include tubes 536, 537 bent into other shapes, such as S-shaped portions or the like.

The U-shaped portions 538 of the tubes 536, 537 may be made of material that is the same or similar to the rest of the tubes 536, 537. Some embodiments may include U-shaped portions 538 that are made of a different material than the rest of the tubes 536, 537. For example, some embodiments may include U-shaped portions 538 that are made of an elastomeric material. A U-shaped portion 538 made of an elastomeric material, for example rubber, may absorb vibrations to a greater degree than more rigid materials such as plastics and the like.

Three different configurations of tubes 540 configured to absorb vibrations are illustrated in FIGS. 16A through 16C. FIG. 16A illustrates a tube 540 having a flexible portion 542. The flexible portion 542 may be made of an elastomeric material such as silicone, rubber, or the like. FIG. 16B illustrates a tube 540 that includes a U-shaped portion 544 similar to those U-shaped portions 538 illustrated in FIG. 15. The U-shaped portion 544 may be made of material similar to the rest of the tube 540 or it may be made of elastomeric material such as silicone, rubber, or the like. FIG. 16C illustrates a tube 540 that includes 90-degree bent portions 546, in order to accomplish the same vibration absorption capacity of the tubes 540 described above. Again, the bent portions 546 may be made of material similar to the rest of the tube 540 or may be made of elastomeric material such as silicone, rubber, or the like.

In addition to the absorption mechanisms described above, which may be disposed between the inner housing 518 and outer housing 520, additional absorption mechanisms may be disposed on an outside surface of the outer housing 520. The smoke evacuation system 400 may be placed on a support surface, such as a table or countertop when in use. Vibration of the outer housing, due to the operation of internal components of the system 400 such as the motor 412 and/or pump 410, may cause the entire system 400 to bounce/travel along the support surface.

Additional vibration absorption mechanisms may be disposed on a bottom outside surface of the outer housing 520 to act as an interface between the smoke evacuation system 400 and the support surface on which the outer housing 520 is placed in order to reduce this effect. The vibration absorption mechanisms may act to absorb the vibrations so the vibrations are not substantially transferred to the support surface. The vibrations absorption mechanisms may also provide greater friction between the outer housing 520 and a support surface to reduce travel along the surface due to vibrations.

Figure 17A:
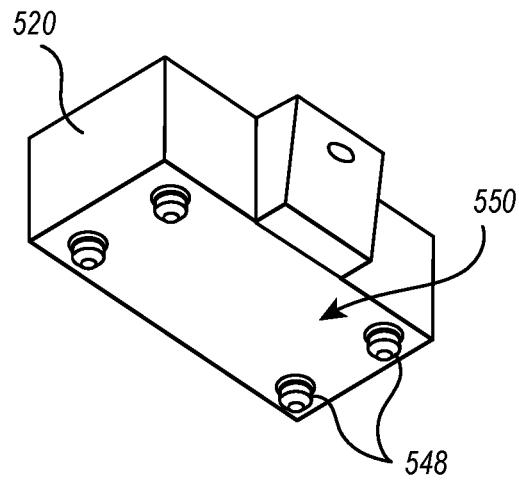
FIG. 17A illustrates one embodiment of a vibration absorption mechanism.

FIG. 17A shows an outer housing 520 that includes a number of feet 548. These feet 548 are vibration absorption mechanisms. The feet 548 are disposed on a bottom surface 550 of the outer housing 520 and may act as an interface between the outer housing 520 and a support surface on which the outer housing 520 is placed. The embodiment illustrated in FIG. 17A includes four feet 548 disposed on the bottom surface 550. Other embodiments may include more or less than four feet 548 that may be arranged in any number of configurations. For example, one embodiment may include only three feet 548. Other embodiments may include five or more feet 548 with some of the feet 548 disposed near the center of the bottom surface 550 as well as the corners.

Figure 17B:
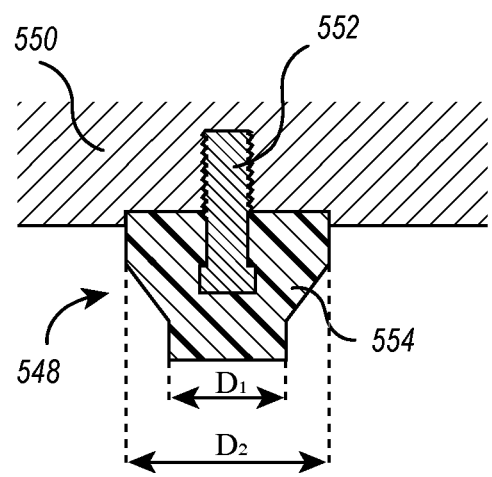
FIG. 17B illustrates a cross-sectional view of one of the vibration absorption mechanisms illustrated in FIG. 17A.

FIG. 17B illustrates a cross-sectional view of one of the feet 548 illustrated in FIG. 17A. The foot 548 may be comprised of a flexible matrix 554 secured to the bottom surface 550 via a rigid or semi-rigid bolt 552. The bolt 552 may be threaded or otherwise secured to the bottom surface 550. The bolt 552 may protrude beyond the bottom surface 550 and the flexible matrix 554 may be molded around the protrusion of the bolt 552.

The flexible matrix 554 of the foot 548 may have a first diameter $D_1$ and a second diameter $D_2$. The first diameter $D_1$ and the second diameter $D_2$ may vary in size. The first diameter $D_1$ may be smaller than the second diameter $D_2$. A contact pressure between the foot 548 and a support surface may increase as the diameter of the foot 548 decreases. Also, certain diameters may absorb a given range of vibrational frequencies better than others. It may therefore be advantageous to vary the diameter of the foot 548 as shown in FIG. 17B.

For example, $D_1$ may absorb a first frequency of vibrations, or first range of frequencies, and $D_2$ may absorb a second frequency of vibrations, or second range of frequencies. Therefore, having a foot 548, such as the foot 548 illustrated in FIG. 17C, with various diameters $D_1$. $D_2$ may enable the foot 548 to substantially absorb both the first and second frequencies, or ranges thereof. One will appreciate that other embodiments may include feet with any number and combination of different diameters to meet the specific range of frequencies being absorbed.

Figure 17C:
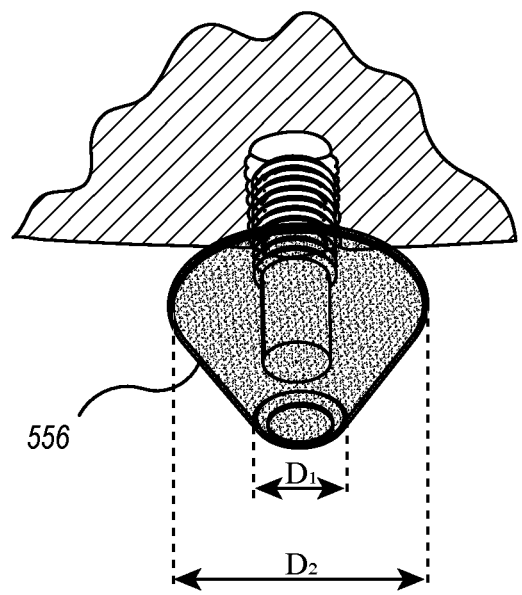
FIG. 17C illustrates one embodiment of a vibration absorption mechanism.

FIG. 17C shows another embodiment of a foot 548 that includes a first diameter $D_1$ that is smaller than a second diameter $D_2$. In this embodiment, the edge profile 556 of the foot 548 is straight so that the foot 548 substantially resembled an inverse cone. Other embodiments may include edge profiles 556 that result in various other shapes.

It will be appreciated that the feet 548 may be secured to the bottom surface 550 in a variety of ways. For example, in one embodiment, the feet 548 may be secured via hooks, nails, adhesives, or the like, without the need for a bolt 552 as shown in FIG. 17B. The feet 548, including other embodiments of feet described herein, may be made of an elastomeric material, such as rubber, silicone, or the like. The elastomeric material of the flexible matrix 554 may absorb vibrations from the outer housing 520 and provide added friction between the bottom surface 550 of the outer housing 520 and a support surface on which the outer housing 520 is placed.

Figure 18A:
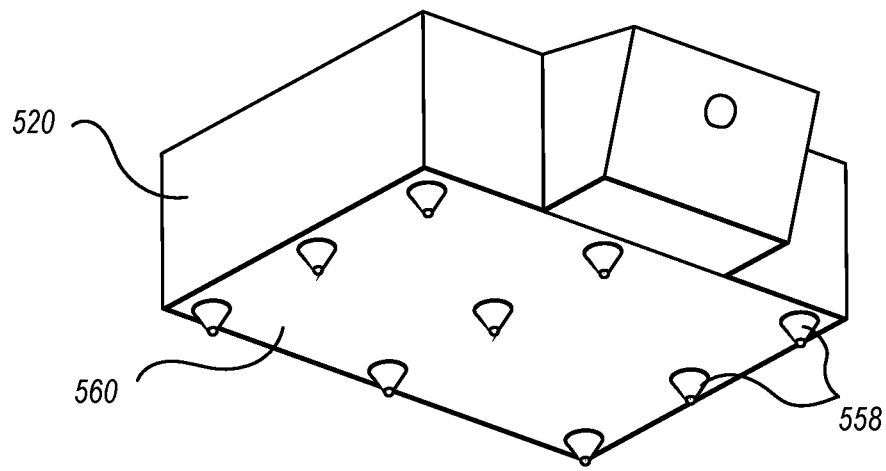
FIG. 18A illustrates one embodiment of a vibration absorption mechanism.

FIG. 18A illustrates a number of feet 558 disposed on the bottom surface 560 of an outer housing 520. In this embodiment, nine feet 558 serve as an interface between the bottom surface 560 and a support surface. Increasing the number of feet 558 may increase the vibration absorption capacity of the system. It may also increase the friction between the bottom surface 560 of the outer housing 520 and a support surface to minimize vibrational travel. Other embodiments may include more than nine feet 558 disposed on the bottom surface 560 in order to increase friction and vibration absorption capacity.

Figure 18B:
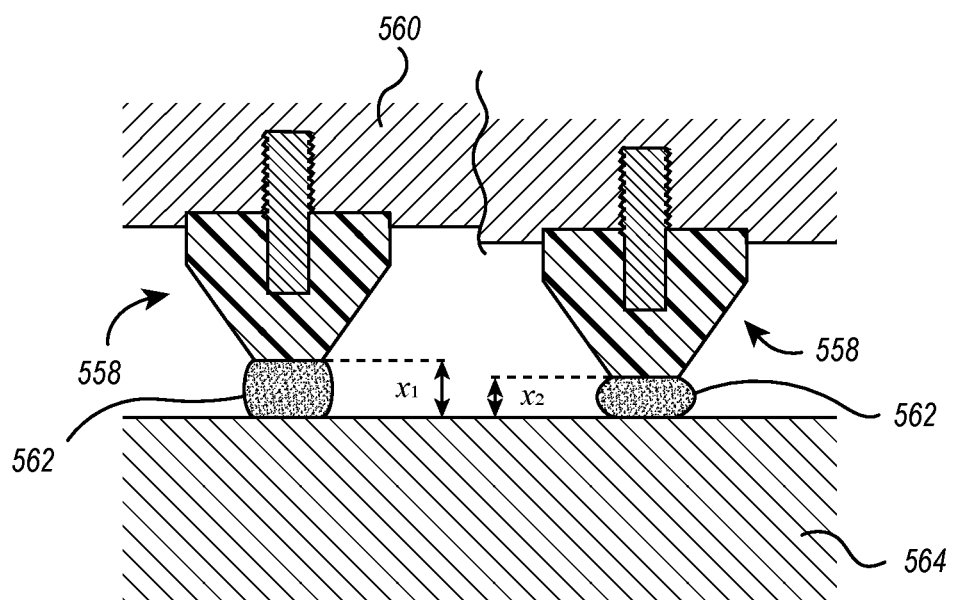
FIG. 18B illustrates a cross-sectional view of the vibration absorption mechanisms illustrated in FIG. 18A.

FIG. 18B illustrates a cross-sectional view of two of the feet 558 shown in FIG. 18A. There may be slight variations in the bottom surface 560 of the outer housing 520 and/or the support surface 564 that cause the surfaces 560, 564 to be uneven. This may result in inconsistent contact between some of the feet 558 and the support surface 564. Flexible spacers 562 may be disposed on the feet 558 to compensate for uneven surfaces 560, 564 so that all the feet 558 may be in contact with the support surface 564 despite unevenness.

As shown in FIG. 18B, the spacers 562 may compress from a first thickness $X_1$ to a second thickness $X_2$. The spacers 562 may be made of an elastomeric material, such as silicone or rubber, so that the thickness X of the spacer 562 may vary depending on the unevenness of the support surface 564 on which the outer housing 520 is placed. In this way, all of the feet 558 may be in contact with the support surface 564 in order to increase vibration absorption capability and friction between the bottom surface 560 and the support surface 564. The spacers 562 may also prevent the outer housing 520 from rocking due to a space or gap between the feet and the support surface.

Figure 19A:
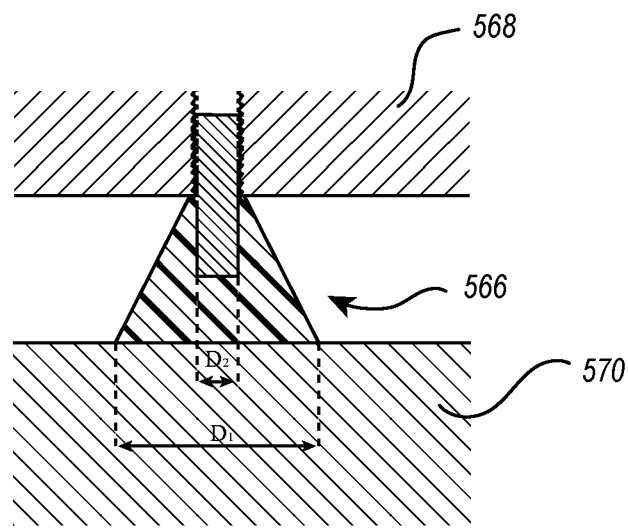
FIG. 19A illustrates a cross-sectional view of one embodiment of a vibration absorption mechanism.
Figure 19B:
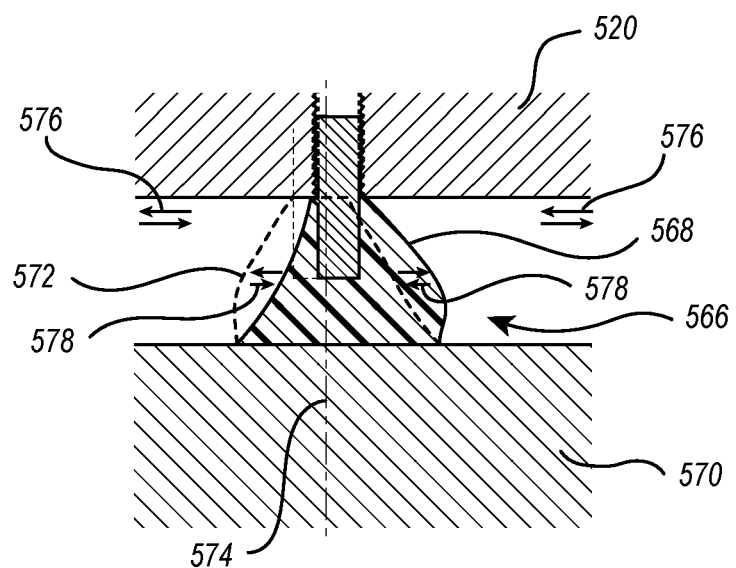
FIG. 19B illustrates the vibration absorption mechanism illustrated in FIG. 19A, but undergoing deformation due to vibrations.

FIG. 19A shows a cross-sectional view of one embodiment of a foot 566 for absorbing vibrations. This embodiment is similar to the embodiment illustrated in FIG. 17C, except here the first diameter $D_1$ is greater than the second diameter $D_2$. FIG. 19B illustrates how the foot 566, which may be comprised of an elastomeric material, may deform due to vibrations in the outer housing 520. As shown, vibrational movements of the outer housing 520, illustrated by arrows 576, are transferred to the foot 566. The foot 566 may laterally deform, as illustrated by arrows 578, from a first shape 572 to a second shape 568. This lateral deformation and/or change in shape of the foot 566 may occur while the interface 574 between the foot 566 and the support surface remains substantially constant. In this way, the foot 566 may absorb vibrations without substantially transferring them to the support surface 570 or traveling across the support surface 570.

The various embodiments of vibration absorption mechanisms described herein, including vibration absorption mechanisms disposed between inner and outer housings, flexible tubing, U-shaped tubing, and feet disposed on a bottom surface of the outer housing, may be employed singly or together in a multitude of combinations. These embodiments may also be included within various embodiments of a smoke evacuation system that includes various types of pumps, blowers, and/or compressors. The vibration absorption mechanisms described herein, combined with pumps that reduce vibrations and noise, may provide a substantial decrease in vibrations and noise inherent in typical smoke evacuation systems.

Motors and Methods of Control

The smoke evacuation system 400 illustrated in FIG. 2 includes motor 412 engaging the pump 410. The motor may rotate a rotary shaft of the various pumps 410 described herein. In one embodiment, the motor 412 may be a permanent magnet synchronous motor. Other embodiments may include a brushless DC motor. Brushless motors may have large starting torques from a fully stopped condition for use with the various pumps described herein. Brushless motors may also have less noise, greater dynamic response, and better speed-vs.-torque characteristics than brushed motors.

The pump 410 may create a pressure differential between a gas entering the pump 410 and a gas exiting the pump 410, as described above. This pressure differential, or compression ratio of the pump 410 may result in a high starting torque of the motor 412 in order to initiate the motor 412 rotating the pump 410.

Motor control methods may be employed to reduce the vibrations and increase motor efficiency and lifespan. Unwanted debris from the outside environment may inadvertently enter the airflow path 408 and cause clogging and/or blockages. These blockages within the system can cause pump and airflow path resistance pressures to rise as airflow is impeded. In order to maintain necessary airflow while blockages are present, pumps and/or motors may need more power and/or speed in order to compensate. Increased speed and/or power may diminish the efficiency of the motor and pump as well as decrease their lifespan. Various control methods of a smoke evacuation system, particularly methods of motor regulation, as described herein, may maintain airflow rates, increase motor efficiency, and preserve the lifespan of the motor and/or pump, especially when blockages and/or clogging of the system occurs.

Figure 20:
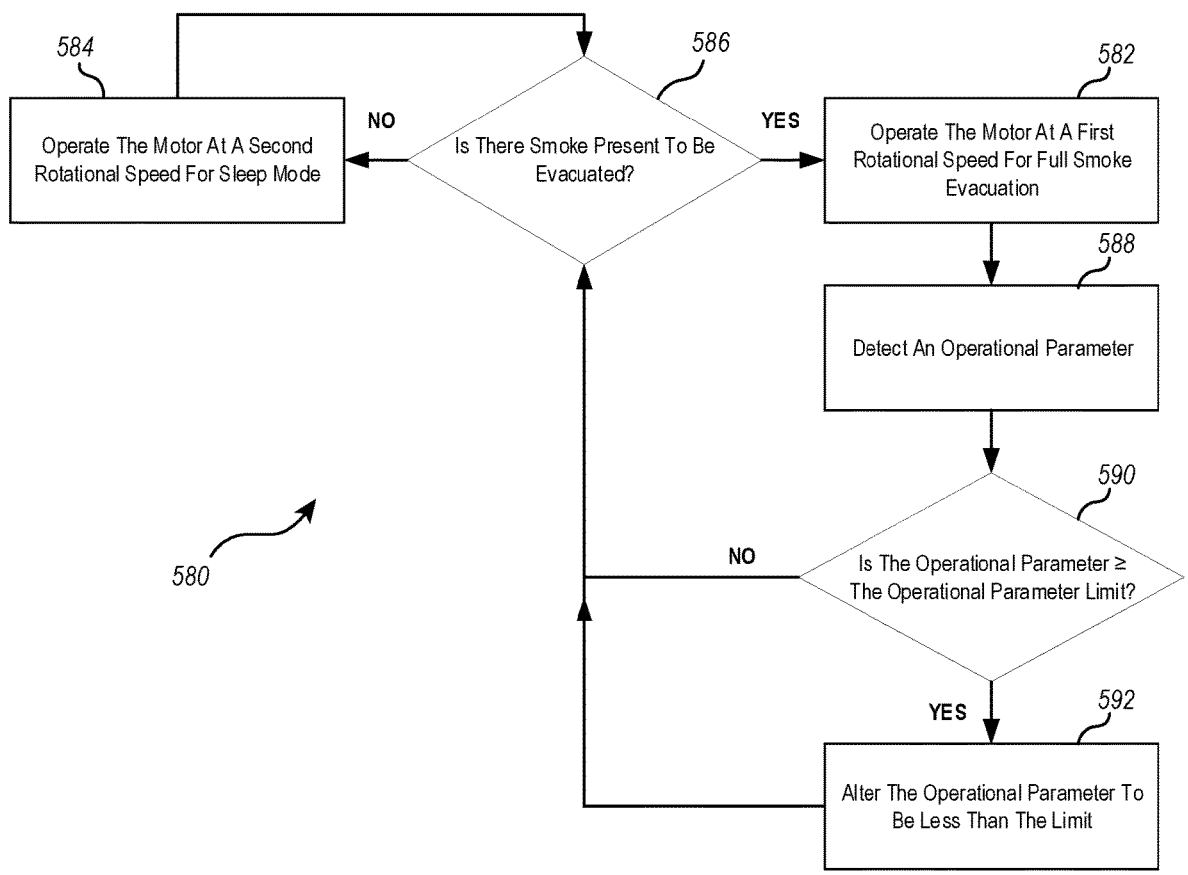
FIG. 20 illustrates a flowchart showing a method of reducing noise and vibration of a smoke evacuation system.

A method 580 for regulating the motor to reduce noise and vibration in a smoke evacuation system is shown in FIG. 20. In a first step 586, the system may sense or detect whether smoke is present to be evacuated or not. This detection may be done automatically when the practitioner begins cutting a patient during electrosurgery, or a separate smoke sensor may be employed to detect smoke present at cutting site. If smoke is present to be evacuated, then a next step 582 of the method may be to regulate the motor so that the rotational speed of the motor results in full smoke evacuation. If no smoke is present to be evacuated, then the next step may be to regulate the motor to operate at a rotational speed so that the motor is in sleep mode 584.

In one embodiment, a method of regulating the motor may include varying a supply of electrical current to the motor. For instance, the method 580 may include supplying a first amount of current to the motor to cause the motor to operate at a first performance level. Alternatively, a second amount of current may be supplied to the motor to cause the motor to operate at a second performance level. The supply of current may be accomplished by varying a pulse width modulation (PWM) duty cycle of an electrical input to the motor. In other embodiments, the current may be varied by adjusting the frequency of the current supplied to the motor. The motor may be engaged with a rotary mechanism, such as the compressors and blowers described above, so that reducing the duty cycle or frequency of a current input to the motor decreases the rotational speed of the rotary mechanism.

In one embodiment, a regulation of the motor may depend on an initial condition, such as the rotational speed of the rotary mechanism. For example, once the system is running, the regulation of the motor may operate the motor at a constant speed that equals the initial rotational speed of the motor. In one embodiment, the first performance level of the motor may result in a first rotational speed of a rotary shaft of the motor engaging a rotary mechanism. The first performance level therefore, may result in a faster rotation of the rotary mechanism. This first performance level, and corresponding rotation speed of the rotary mechanism, may be the speed needed for normal suction of a gas through the airflow path. A second performance level may be slower than the first so that the second performance level causes the rotary mechanism to operate at a speed lower than the first level.

The first performance level may be employed when there is no smoke produced by the electrosurgical instrument, but it is advantageous to keep the smoke evacuation system active. For example, a practitioner performing electro-surgery may temporarily have no need to suck smoke into the system to be filtered because the practitioner is not currently cutting the flesh of the patient and producing smoke. Instead of completely turning off the smoke evacuation system every time smoke is not being produced, and suction is temporarily not needed, the motor may switch to the second, slower performance level.

When the practitioner begins cutting again with the electrosurgical instrument, producing unwanted smoke, the motor may be switched back to the first, higher performance level, thus creating a higher vacuum pressure necessary to suck smoke into the system to be filtered. This lower second performance level may be thought of as a sleep mode. In sleep mode, the motor may still run, but not to its full or usual strength/rotational speed. The sleep mode may preserve the lifespan of the motor, and/or rotary mechanism with which it is engaged, by reducing the stress and wear caused by running the motor at full capacity at all times.

The second, lower performance level of the motor may be more advantageous than turning the motor completely off when suction is not needed, and switching the motor on when suction is needed. This is because a practitioner may need to use the suction only intermittently during long periods of surgery. Turning a motor on from a completely turned-off state requires high start-up torques in order to overcome the standstill inertia of the motor. Repeatedly turning the motor on from a completely off mode in this manner is inefficient and may decrease the lifespan of the motor. Alternatively, employing a sleep mode as described above, with a first and second performance level, allows the motor to remain on during intermittent non-use of the system during surgery, so that activation of the first performance level when suction is needed can be done without the higher torques needed to overcome standstill inertia.

In one embodiment, a method of motor control may be employed to limit substantial overheating of the motor. The motor may overheat if a blockage in the airflow path of the smoke evacuation system causes an overworking of the motor and/or rotary mechanism as they attempt to compensate for the blockage and maintain a constant airflow rate. Therefore, in the method 580 for regulating the motor, a further step may include detecting an operational parameter. The operational parameter may be, but is not limited to, the temperature of the motor and/or rotary mechanism and/or the pressure in the airflow path of the smoke evacuation system.

In one embodiment, the next step 590 may be to compare the detected operational parameter to an operational parameter limit. This parameter limit may be preset. If the detected operational parameter is greater than or equal to the operational parameter limit, the next step 592 of the method may include altering the operational parameter to be less than the operational parameter limit. In one embodiment, the method may include setting a temperature limit and sensing a temperature of the motor and/or rotary mechanism. When the temperature of the motor and/or the rotary mechanism is equal to or greater than the temperature limit, the motor may be shut off or its performance level reduced.

In one embodiment, the method may include defining a pressure limit and sensing a pressure within the circulation path of the rotary mechanism and/or the airflow path of the smoke evacuation system. A pressure inside the airflow path or rotary mechanism may increase when blockage occurs inside the airflow path as described above. In order to prevent the motor from overextending itself to overcome these higher pressures, the motor may be shut off or its performance level reduced, as described above, when the sensed pressure is equal to or greater than the set pressure limit. In one embodiment, the method may include disengaging the motor from the rotary mechanism. The motor may disengage from the rotary mechanism via a clutch.

In one embodiment, the method may include manipulating one or more orifices disposed near the motor within the airflow path of the smoke evacuation system. This method may also include defining a pressure limit and sensing a pressure within the airflow path as described above. When the sensed pressure is equal to or greater than the pressure limit, the one or more orifices may be opened to allow air to flow from inside the otherwise closed airflow path of the system to the surrounding environment, or vice versa. Opening the one or more orifices may reduce the pressure within the system, thus preventing the motor and/or rotary mechanism from attempting to compensate for the higher pressure.

The various methods of regulating the motor and or smoke evacuation system described herein may be employed in conjunction with any of the embodiments of a smoke evacuation system described above. These methods may also be employed independent of the various other embodiments.

The present invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. A smoke evacuation assembly comprising:
   a filter;
   a dual scroll pump having a sealed positive displacement airflow path, the dual scroll pump comprising:
      a first scroll pump comprising a moving scroll and a stator scroll, the moving scroll being configured to rotate in a first direction; and
      a second scroll pump comprising a moving scroll and a stator scroll, the moving scroll being configured to rotate in a second direction that is opposite to the first direction,
      wherein the dual scroll pump has a first operating pressure and a second operating pressure, and wherein a first flow rate of a gas flowing through the sealed positive displacement airflow path at the first operating pressure is the same as a second flow rate of a gas flowing through the sealed positive displacement airflow path at the second operating pressure, and wherein a difference in pressure between the first operating pressure and the second operating pressure is equal to or greater than 1.5 psig; and
   a motor engaging the dual scroll pump to rotate the moving scrolls.

2. The smoke evacuation assembly of claim 1, wherein the first scroll pump and the second scroll pump are arranged in parallel to one another.

3. The smoke evacuation assembly of claim 1, wherein the first scroll pump and the second scroll pump are arranged in series with one another.

4. The smoke evacuation assembly of claim 1, further comprising:
   a first housing at least partially surrounding the smoke evacuation assembly;
   a second housing at least partially surrounding the motor and the dual scroll pump;
   an interface between the first housing and the second housing comprising one or more vibration absorption mechanisms; and
   one or more vibration absorption mechanisms disposed on a bottom outer surface of the first housing.

5. The smoke evacuation assembly of claim 1, wherein the first scroll pump and the second scroll pump are different sizes from one another.

6. The smoke evacuation assembly of claim 1, wherein the airflow path comprises one or more at least partially flexible tubes, wherein at least one at least partially flexible tube of the one or more at least partially flexible tubes is disposed between the filter and the dual scroll pump.

7. The smoke evacuation assembly of claim 6, further comprising an exhaust mechanism, wherein at least one at least partially flexible tube of the one or more at least partially flexible tubes is disposed between the dual scroll pump and the exhaust mechanism.

8. A smoke evacuation system comprising:
a filter;
a dual scroll pump configured to draw a gas through the filter, the dual scroll pump comprising:
  a first scroll pump comprising a moving scroll and a stator scroll, the first scroll pump being of a first size; and
  a second scroll pump comprising a moving scroll and a stator scroll, the second scroll pump being of a second size that is larger than the first size of the first scroll pump,
wherein the dual scroll pump has a first operating pressure and a second operating pressure, and wherein a first flow rate of a gas at the first operating pressure is the same as a second flow rate of a gas flowing at the second operating pressure, and wherein a difference in pressure between the first operating pressure and the second operating pressure is equal to or greater than 1.5 psig; and
one or more motors engaged with the dual scroll pump and configured to rotate the moving scrolls,
wherein the first scroll pump is configured to provide a constant low-level airflow over time and the second scroll pump is configured to provide a higher airflow over time.

9. The smoke evacuation system of claim 8, wherein the moving scroll of the first scroll pump is configured to rotate in a first direction.

10. The smoke evacuation system of claim 9, wherein the moving scroll of the second scroll pump is configured to rotate in a second direction that is opposite to the first direction.

11. The smoke evacuation system of claim 8, wherein the first scroll pump and the second scroll pump are arranged in parallel to one another.

12. The smoke evacuation system of claim 11, wherein the first scroll pump and the second scroll pump are arranged in series with one another.

* * * * *